United States Patent
Tuunanen et al.

(10) Patent No.: US 12,065,698 B2
(45) Date of Patent: Aug. 20, 2024

(54) SAMPLE PROCESSING APPARATUS AND METHOD

(71) Applicant: Thermo Fisher Scientific Baltics UAB, Vilnius (LT)

(72) Inventors: Jukka Tuunanen, Vantaa (FI); Jaako Kurkela, Vantaa (FI); Katja Eklin, Vantaa (FI)

(73) Assignee: Thermo Fisher Scientific Baltics UAB, Vilnius (LT)

(*) Notice: Subject to any disclaimer, the term of this patent is extended or adjusted under 35 U.S.C. 154(b) by 0 days.

(21) Appl. No.: 17/498,308

(22) Filed: Oct. 11, 2021

(65) Prior Publication Data
US 2022/0275447 A1    Sep. 1, 2022

Related U.S. Application Data

(60) Continuation of application No. 16/815,520, filed on Mar. 11, 2020, now abandoned, which is a
(Continued)

(30) Foreign Application Priority Data

Oct. 2, 2009 (FI) ...................................... 20096013

(51) Int. Cl.
*C12Q 1/6876* (2018.01)
*C12Q 1/6844* (2018.01)
(Continued)

(52) U.S. Cl.
CPC ......... *C12Q 1/6876* (2013.01); *C12Q 1/6846* (2013.01); *C12Q 1/686* (2013.01);
(Continued)

(58) Field of Classification Search
CPC .... C12Q 1/6846; C12Q 1/686; C12Q 1/6876; G01N 2021/6439; G01N 21/251; G01N 21/29; G01N 21/6428; G01N 21/78
See application file for complete search history.

(56) References Cited

U.S. PATENT DOCUMENTS 3,957,436 A    5/1976 Murray
4,319,884 A    3/1982 Wilson et al.
(Continued)

FOREIGN PATENT DOCUMENTS

EP    1057653 A1    12/2000
EP    2239338 A1    10/2010
(Continued)

OTHER PUBLICATIONS

Albert et al., "Accuracy Matters When Manually-pipetted PCR Assays Graduate to Automation—A Story in Diagnosing and Troubleshooting," Artel Abstract, (2008).
(Continued)

*Primary Examiner* — Tri T Ton
(74) *Attorney, Agent, or Firm* — McNeill Baur PLLC

(57) ABSTRACT

The invention relates to a sample processing apparatus comprising a holder for a microtiter plate comprising a plurality of microwells, optical measurement unit for measuring optical responses of samples dosed to the microwells, and a computing unit configured to analyze the optical responses in order to detect dosing failures in said plurality of microwells, and if a dosing failure has been detected in one or more of the microwells, to communicate the existence of the dosing failure to a user of the apparatus through signaling means or to store data indicative of the dosing failure to data storage means for further use. In particular, the invention relates to detecting dosing failures in before, during and after a PCR process.

14 Claims, 17 Drawing Sheets

Related U.S. Application Data continuation of application No. 15/989,926, filed on May 25, 2018, now Pat. No. 10,626,461, which is a continuation of application No. 15/210,075, filed on Jul. 14, 2016, now Pat. No. 10,006,086, which is a division of application No. 13/078,720, filed on Apr. 1, 2011, now Pat. No. 9,422,604, said application No. 15/989,926 is a continuation-in-part of application No. PCT/FI2010/050772, filed on Oct. 4, 2010.

(51) Int. Cl.

| | |
|---|---|
| *C12Q 1/686* | (2018.01) |
| *G01N 21/25* | (2006.01) |
| *G01N 21/29* | (2006.01) |
| *G01N 21/64* | (2006.01) |
| *G01N 21/78* | (2006.01) |

(52) U.S. Cl.
CPC ........... *G01N 21/251* (2013.01); *G01N 21/29* (2013.01); *G01N 21/6428* (2013.01); *G01N 21/78* (2013.01); *G01N 2021/6439* (2013.01)

(56) References Cited

U.S. PATENT DOCUMENTS

| | | | |
|---|---|---|---|
| 4,354,376 A | 10/1982 | Greenfield et al. | |
| 5,565,339 A | 10/1996 | Bloch et al. | |
| 5,861,251 A | 1/1999 | Park et al. | |
| 6,153,412 A | 11/2000 | Park et al. | |
| 6,350,588 B1 | 2/2002 | Roth et al. | |
| 6,372,424 B1* | 4/2002 | Brow ................ | C12N 15/113 435/6.12 |
| 6,741,365 B2 | 5/2004 | Curtis | |
| 6,825,921 B1 | 11/2004 | Modlin et al. | |
| 6,942,964 B1 | 9/2005 | Ward et al. | |
| 6,952,259 B2 | 10/2005 | Pible et al. | |
| 7,404,930 B2* | 7/2008 | Fouillet ............ | G01N 35/00009 422/50 |
| 8,663,925 B2 | 3/2014 | Kurkela et al. | |
| 9,416,417 B2 | 8/2016 | Kurkela et al. | |
| 9,422,604 B2* | 8/2016 | Tuunanen ............ | C12Q 1/686 |
| 10,006,086 B2 | 6/2018 | Tuunanen et al. | |
| 2003/0146115 A1 | 8/2003 | Sharp | |
| 2004/0091916 A1* | 5/2004 | Vandezande ........... | G16B 40/00 435/6.16 |
| 2004/0246501 A1 | 12/2004 | Curtis | |
| 2005/0148011 A1* | 7/2005 | Ward ................ | C12Q 1/6813 435/7.1 |
| 2006/0039000 A1 | 2/2006 | Sacchi | |
| 2006/0110748 A1* | 5/2006 | Sorge ................ | C12Q 1/6844 435/6.1 |
| 2006/0183115 A1* | 8/2006 | Wang ................ | C12Q 1/683 435/6.12 |
| 2006/0228801 A1 | 10/2006 | Fryer et al. | |
| 2007/0015169 A1 | 1/2007 | Jia et al. | |
| 2007/0141709 A1 | 6/2007 | Albert et al. | |
| 2008/0295258 A1* | 12/2008 | Allen ................ | D06B 23/205 428/85 |
| 2010/0159448 A1 | 6/2010 | Gonzalez et al. | |
| 2010/0159488 A1 | 6/2010 | Drancourt et al. | |
| 2010/0258742 A1 | 10/2010 | Heindl et al. | |
| 2011/0045992 A1* | 2/2011 | Shao ................ | C12Q 1/6874 506/7 |
| 2011/0086337 A1 | 4/2011 | Sagner et al. | |
| 2011/0251080 A1 | 10/2011 | Tuunanen et al. | |
| 2012/0034594 A1* | 2/2012 | Semrau ............. | C07D 413/12 530/323 |
| 2012/0237924 A1* | 9/2012 | Wang ................ | C12Q 1/6848 435/6.1 |
| 2016/0265014 A1* | 9/2016 | Wangh ............... | C12Q 1/6848 |
| 2016/0312268 A1 | 10/2016 | Kurkela et al. | |
| 2017/0009291 A1 | 1/2017 | Tuunanen et al. | |
| 2018/0355428 A1 | 12/2018 | Tuunanen et al. | |
| 2019/0187031 A1* | 6/2019 | Johnson-Buck ......... | C07K 1/14 |
| 2021/0348218 A1* | 11/2021 | Sardar ................ | G01N 21/658 |
| 2021/0396747 A1* | 12/2021 | Singamaneni ... | G01N 33/54373 |

FOREIGN PATENT DOCUMENTS

| | | |
|---|---|---|
| FR | 2918754 A1 | 1/2009 |
| JP | S53142521 A | 12/1978 |
| JP | 2010243497 A | 10/2010 |
| JP | 2010252790 A | 11/2010 |
| KR | 20020045167 A | 6/2002 |
| WO | 1995006137 A1 | 3/1995 |
| WO | 9533839 A1 | 12/1995 |
| WO | 1996013225 A2 | 5/1996 |
| WO | 2007088506 A2 | 8/2007 |
| WO | 2007137291 A1 | 11/2007 |
| WO | 2008033521 A2 | 3/2008 |
| WO | 2008042960 A2 | 4/2008 |
| WO | 2011039425 A1 | 4/2011 |

OTHER PUBLICATIONS

Bustin, S., "A-Z of Quantitative PCR," Intl Univ. Line, La Jolla, CA., 2009, pp. 580-581, p. 827.
Correa et al., Chapter 6, "Small Molecule-Based Fret Probes," in Gadella, Ed., Fret and Film Techniques, 2008, p. 245.
English Machine Translation of FR 2 918 754, dated Jan. 16, 2009 (5 pages).
English version of the bibliographic data and machine translation of the description for Japanese Publication No. JP-S53-142521 A.
File History of U.S. Appl. No. 13/078,720, filed Apr. 1, 2011.
File History of U.S. Appl. No. 13/499,518, filed May 10, 2015.
File History of U.S. Appl. No. 14/195,088, filed Mar. 3, 2014.
File History of U.S. Appl. No. 15/139,738, filed Apr. 27, 2016.
File History of U.S. Appl. No. 15/210,075, filed Jul. 14, 2016.
File History of U.S. Appl. No. 15/989,926, filed May 25, 2018.
File History of U.S. Appl. No. 16/815, 520, filed Mar. 11, 2020.
International Preliminary Report on Patentability, PCT/FI2010/050772, mailed Apr. 3, 2012, 6 pages.
International Search Report and Written Opinion for PCT/FI2010/050772, mailed Feb. 10, 2011, 8 pages.
Opposition against EP2483422, filed Sep. 3, 2014, 31 pages.
Potter et al. "Development and Evaluation of Passive Reference Candidate Compounds for Normalization of Signal in Real-Time PCR," available at https://www.biosearchtech.com/assets/bti_passive_reference.pdf, Oct. 27, 2004.
Sanis et al., "Malachite Green," Handbook of Biological Dyes and Stains, 2010, pp. 286-287.
Sanis et al., "Methylene Blue," Handbook of Biological Dyes and Stains, 2010, pp. 293-295.
Soots, et al., "Basic Biotechnology Kit: Micropipet Technique," Biotechnology in the Classroom, Univ. of Calif. Davis, 2009, 7 pages.
"Thermo Scientific ABsolute Blue Master Mixes," Thermo Fisher Scientific Inc., 2008, 3 Pages.
European Application No. 10777044.8, Intention to Grant for European Patent Office, May 23, 2013, 5 Pages.
English translation of Official Action issued in Japanese Application No. 2012-531466, dated Dec. 4, 2014, by Shinya Yamamoto, 4 pages.
Opposition against EP2483422 from Nederlandsch Octroobibureau, submitted Sep. 3, 2014, 29 Pages.
PCT/FI2012/050318, International Search Report and Written Opinion, Jul. 11, 2012, 16 Pages.
Tan, H.Y., et al., "Absorbance and Fluorometric Sensing with Capillary Wells Microplates," Review of Scientific Instruments, Dec. 2, 2010, vol. 81, No. 124301, 6 Pages.

* cited by examiner

SAMPLE PROCESSING APPARATUS AND METHOD

This application is a divisional of U.S. application Ser. No. 16/815,520, filed Mar. 11, 2020, which is a continuation of U.S. application Ser. No. 15/989,926, filed May 25, 2018, which is a divisional of U.S. application Ser. No. 15/210,075, filed Jul. 14, 2016, which is a divisional of U.S. application Ser. No. 13/078,720, filed Apr. 1, 2011, which is a Continuation-in-part of PCT International Application No. PCT/FI2010/050772, filed Oct. 4, 2010, which designated the United States and which claims priority to Finnish Application No. 20096013, filed Oct. 2, 2009, the entire contents of all of which are hereby incorporated by reference and for which priority is claimed under 35 U.S.C. §§ 119-120.

FIELD OF THE INVENTION

The invention relates to detection of sample dosing failures in (bio)chemical assays In particular, the invention relates to a method of detecting pipetting failures in multicomponent assays, such as Polymerase Chain Reaction (PCR) amplification, in particular quantitative PCR (qPCR) amplification.

BACKGROUND OF THE INVENTION

When pipetting the PCR reaction, all necessary components, i.e. reagents, can be added to the reaction tube one by one, or preferably by first combining at least some of them as a master mix followed by dividing this mixture to multiple samples. One of the components that usually must be added separately is the sample under study. The number of samples, tubes or sample wells in a microtiter plate can be hundreds or even thousands per setup.

Adding reagents correctly, i.e. in the right order and amount, is crucial for obtaining valid results not only in PCR but also in many other (bio)chemical reactions. Failed experiments result in loss of time and money. Economical importance can be huge. This is because of waste of ingredients, plastic ware and personnel working hours. Moreover, delays in obtaining the results of the experiments may be significant. There have been various solutions to this well-known problem.

There are mechanical solutions to the problem. The art acknowledges various automated pipetting robots, multichannel pipettes and guidance systems (e.g. Finnzymes Piko® Light Plate, BioTx Well Aware™) used with sample tubes and plates.

For several years there have also been available PCR master mixes or buffers that contain some visible dye to help pipetting and tracking of electrophoresis runs. These mixes typically also have some component to increase density of the solution to help in electrophoresis gel loading.

U.S. Pat. No. 6,942,964 discloses a product using a pipetting aid dye which is also used as a gel loading and tracking dye. The colorant has been incorporated with the polymerase, which helps the user to see whether the polymerase has been pipetted to the PCR mix or master mix. A similar product is BioLine Accuzyme Red.

USB Corporation's RubyTaq features a polymerase including a mixture of two dyes which are separated during the agarose gel run: magenta (runs between 500 bp [2% gels] and 1500 bp [0.8% gels]) and yellow (runs less than 10 bp).

Fermentas and Promega have also added a colorant to the enzyme reaction buffer. Fermentas' DreamTaq™ Green reaction buffer can be seen as green, but the color separates into a blue and yellow bands during gel electrophoresis. Promega GoTaq and GoTaq Green Mastermix behave similarly.

There are also products available where the dye added to the polymerase is not intended to help in the electrophoresis phase. Examples include ABgene Red® Hot.

NEB provides a product (Crimson Taq) featuring a dye Acid red added to the DNA polymerase reaction buffer. The product also uses 6% dextran as a density enhancer.

Qiagen's CoralLoad dye is available both as a concentrate in a separate tube, for being added to an uncolored master mix, and also as an optional ready-made 10× PCR buffer. It contains two gel tracking dyes (orange and red).

KR 2002/0045167 discloses freeze-dried PCR mixes containing a colorant to confirm dissolution of the PCR components. U.S. Pat. No. 6,153,412 discloses also freeze-died reaction mixtures which are used for identifying the existence of a lyophilized PCR reagent and to ensure complete mixing of the PCR reagent and the test sample. U.S. Pat. No. 5,565,339, on the other hand, discloses the use of a dye in a hot start wax, which does not dissolve into the reaction mixture. Absolute Blue QPCR Master Mix contains an inert blue dye to ease pipetting in reaction set-up.

Also WO 2007/088506 discloses a dyed master mix.

Applied biosystems has ROX passive reference dye included in their qPCR products. The purpose of the dye is to provide a steady fluorescence level which can be used to normalize against any non PCR related fluorescence variation between the different reactions and in one sample during a reaction. The method is also suggested to normalize at least partly against deviations in pipetting accuracy.

All but the three last ones of the products mentioned above are suggested to be used only in traditional end point PCR. In addition to the colorants, they typically contain a density enhancer to get the sample material into the bottom of the gel wells (see e.g. U.S. Pat. No. 6,942,964). Without the density enhancer, samples would disperse into the surrounding liquid.

Colorants used in end-point PCR are generally not compatible with quantitative PCR (qPCR). This is usually because they prevent real-time optical measurements of the ongoing reaction. In particular, the dyes typically have a spectrum which overlaps with the detection wavelengths of qPCR fluorescence or their absorbance is too high. General requirements for the dyes used include non-inhibitory effect on the PCR reaction or stability in the reaction pH.

An additional disadvantage of the abovementioned solutions in which the dye is provided in the master mix or in the polymerase is that they are not able to provide help for pipetting the samples (i.e. in PCR the material to be amplified). Sample pipetting is, however, the step where keeping track of the process is most important—and most difficult.

Neither the various mechanical systems available cannot solve the problem entirely. They are expensive and pipetting errors cannot always be seen visually mainly because of volume differences, which means the error might not be detected until after obtaining failed results.

Thus, there is a need for enhanced pipetting aids. In particular, there is a need for such pipetting aids which can be applied also for the sample pipetting phase.

SUMMARY OF THE INVENTION

It is an aim of the invention to provide a novel sample processing apparatus and sample processing method for detecting dosing failures which may occur during pipetting, in particular. One specific aim is to make the detection of errors easier in various stages of pipetting when preparing multi-component assays, for example PCR assays.

The aims of the invention are achieved by the invention as hereinafter described and claimed.

The sample processing apparatus according to the invention comprises a holder for a microtiter plate comprising a plurality of microwells, optical measurement unit for measuring optical responses of samples dosed to microwells, a computing unit configured to analyse the optical responses in order to detect dosing failures in said plurality of microwells, and, if a dosing failure has been detected in one or more of the microwells, to communicate the existence of the dosing failure to a user of the apparatus through signaling means or to store data indicative of the dosing failure to data storage means for further use.

According to one embodiment, the optical measurement unit is capable of spectral resolution and the computing unit is configured to determine whether the the spectral response of the samples meet predefined criteria of a dosing failure.

According to one embodiment, the optical measurement unit is capable of measuring the optical absorption of the samples. Thus, there may be provided, on one side of the samples, a light source unit, and on the opposing side of the samples, a light detector unit. This embodiment can be used, in particular, if a transparent microtiter plate is used and if there is optical access to the plate both from above and below. In pipetting apparatuses, this condition can be normally satisfied. However, in (q)PCR devices, the presence of a sample heating block, which must be in intimate contact with the microtiter plate below it, may prevent absorbance measurement or require substantial modifications to the PCR device.

According to one embodiment, the optical measurement unit is capable of measuring optical scattering of the samples. Scattering measurement can be performed from one side of the microtiter plate only, typically from above. There may be provided a light source unit and a detector unit at least one of which is arranged to emit or collect light, respectively, at an oblique angle with respect to the microtiter plate (i.e. deviating from the normal axis of the surfaces of the samples). This arrangement has the advantage that potentially harmful reflection from the surface of the samples can be minimized (mostly scattered, not reflected, light is collected).

According to one embodiment the optical measurement unit is capable of measuring the fluorescence of the samples. Fluorescence measurement may further increase the detection accuracy but necessitates the presence of suitable fluorescent agents in the sample.

According to one embodiment, the optical measurement unit comprises a light source unit and a detector unit at least one of which is capable of emitting light or detecting light at multiple wavelength channels. This allows one to perform a colorimetric measurement, i.e., a measurement providing information about the spectral properties of the sample. If only one of said devices is capable of operating at multiple wavelength channels (e.g. narrow-band light sources and single channel detector), colorimetric data can be obtained by performing sub-measurements at each of the channels separately and analyzing the sub-measurement data in the computing unit. If both said devices can operate at a plurality of wavelength channels (e.g. white light source and multichannel detector), the measurement of each microwell or even the whole plate can be performed at one shot.

The optical measurement unit can be adapted to measure the microwells sequentially using a single-head measurement unit or it may comprise a plurality of light sources and/or light detection units for each of the microwells separately but simultaneously. On the other hand, camera-based detection allows for measurement of the whole plate quickly.

According to one embodiment, the optical measurement unit is configured to produce two-dimensional images of the samples in the microwells, and the computing unit is configured to determine, based on said image, whether the surface shape and/or area of the samples meet predefined criteria of a dosing failure. In this embodiment, the well shape of the microtiter plate must be such that the determination is possible, i.e. varying in shape or size in the depth-dimension of the well. Further, based on the image, the computing unit may be configured to determine, based on the surface shape and/or area of the samples, the surface level of the samples in a varying-diameter or varying-shape microwell.

The present automatic sample processing apparatus may be a pipetting or another type liquid dispensing apparatus, whereby it additionally comprises means for (pipetting) dispensing one or more substances to the microwells. Alternatively or additionally, the present sample processing apparatus can be adapted to automatically perform a (bio) chemical process or to analyze the composition of the samples contained in the microwells. In particular, the apparatus can be a PCR apparatus comprising means for performing a PCR process to the contents of the microwells.

The invention can be used for detecting dosing failures in before, during and after a PCR process.

If the apparatus is integrated into a PCR apparatus, it may be configured to perform the optical measurement before, after or both before and after performing the PCR process. If the optical measurement both before and after the PCR process, the computing unit may be adapted to compare the optical responses of the same microwell before and after the PCR process. The measurements can be carried out through a sealing layer which may be attached on top of the microtiter plate in order to prevent spilling and evaporation.

According to one embodiment, the computing unit is adapted to compare the optical responses of two or more different microwells of the same microtiter plate with each other in order to detect the dosing failure. Evaluation based on mutual comparison of the wells may provide sufficient level of certainty in many applications. Additionally, reference data may be used in order to improve certainty.

To be able to be used for widely used PCR processes, the apparatus, in particular plate holder thereof, must be designed to receive microtiter plates with conical, i.e. v-bottomed, microwells. This well shape has proven to be not optimal for absorbance measurement, whereby scattering- or fluorescence-based measurements are preferred.

According to one embodiment, present method for detecting dosing failures in a chemical or biological assay performed in one or more instruments comprises pipetting a first reagent solution comprising at least one substance required for performing said assay to a measurement space, the first reagent solution further comprising first colorant providing the solution a first color, pipetting a second reagent solution comprising at least one other substance required for performing said assay to a measurement space, the second reagent solution further comprising second colorant providing the solution a second color different from the first color, mixing the first and second reagent solutions in the measurement space for providing a mixed solution, the mixed solution having, due to said first and second colorants, a third color different from the first and second colors, measuring the optical response of the mixed solution, analysing the optical response in order to detect a potential pipetting failure, and if a pipetting failure is detected, communicating the existence of the pipetting failure to a user of said one or more instruments or storing data indicative of the pipetting failure in storage space of said one or more instruments.

As concerns the steps starting from the measurement of the optical response, the features discussed with the apparatus above can be applied, accordingly.

The preparation of a PCR sample, as an example of a useful application are of the claimed apparatus and method of the invention, is described below. However, it should be noted that same principles can be applied also for other assays involving mixing of two or more components (multi-component assays).

In the pipetting stage of PCR assays, at least two reagent solutions are mixed for obtaining the final mixture which is subjected to PCR. According to one embodiment the reagent solutions are colored with different initial colorants, which, upon mixing produce a distinguishable color different from the colors of the initial colorants.

Thus, one can tell directly by the color of the solution, whether it is the first reagent solution, the second reagent solution or the mixture of these.

More specifically, the method comprises providing a first reagent solution comprising at least one substance required for performing the assay and a first colorant providing the solution a first color, providing a second reagent solution comprising at least one other substance required for performing said assay and a second colorant providing the solution a second color different from the first color, mixing the first and second reagent solutions for providing a mixed solution to be subjected to the PCR process, the mixed solution having, due to said first and second colorants, a third color different from the first and second colors.

In a typical application, one of the reagent solutions is a sample solution, that is, a solution containing or intended to receive a biological sample to be amplified in the PCR assay, and the other of the reagent solutions contains some other at least one other substance required for performing the assay, for example the polymerase solution or master mix. The sample solution may be a buffered solution (hereinafter "a sample buffer solution"). Thus, a microwell having a first color indicates that there is only sample solution without other reagents, e.g. master mix, in the well. A microwell with second color indicates that master mix has been added but there is no sample yet. Finally, a microwell with third color implies that sample has been properly added to the master mix. The inspection of the color can be made visually or by automatic optical means.

In one embodiment, one of the reagent solutions is an elution buffer, such an elution buffer used in combination with a nucleic acid purification kit.

In one embodiment, one of the reagent solutions is a dilution buffer used to facilitate lysis of a solid-state sample to release nucleic acids. The reagent solution can also be used to dilute, digest or precipitate released components before PCR. Thus, it is possible to use the invention when pipetting direct PCR assays.

In further embodiments, one of the reagent solutions is a solution used in cDNA synthesis reaction, reverse transcriptase reaction or bisulphite reaction.

In one embodiment, one of the reagent solutions is some other solution used for preparing the sample for the PCR process.

The invention also provides a new use of dyes for producing two or more colored PCR reagent solutions, which are capable of forming a mixed solution having a color distinguishable from the initial colors of the reagent solutions.

A particular aim of the invention is to achieve a pipetting aid solution which is compatible with quantitative PCR. This is achieved by using such colorants and colorant concentrations which do not significantly disturb the fluorescent processes, i.e. excitation and emission, or optical detection used in qPCR. In particular, the reaction mixture subjected to qPCR is transparent or translucent at least at the qPCR excitation and emission wavelengths. This generally means that the maximum absorbance of the of the reaction mixture is less than 0.5, in particular less than 0.15 (measured using 1 mm light path) and that the absorption window of the colorant does not overlap, at least significantly, with the excitation or emission wavelengths of the fluorescent qPCR dye(s) or modified DNA oligonucleotide probe(s) used.

In one embodiment, a reaction mixture for quantitative PCR is prepared, the reaction mixture comprising fluorescent dye, primer or probe, and wherein the absorbance peaks of any of said colorants do not overlap with the emission or excitation wavelength of said fluorescent dye, primer or probe. If overlap exists, it should not significantly weaken the qPCR signal, generally implying that the total absorbance of the reaction mixture at said wavelengths is less than 0.05, preferably less than 0.03, in particular less than 0.1.

The invention provides considerable advantages. As the initial solutions and the resultant solution are mutually of different colors, one not only distinguish between the initial solutions, but also between the initial solutions and their mixture.

In addition, from colored solutions one can be quickly perceive whether the solutions have been properly mixed and whether there are significant deviations from the desired reaction volume.

Moreover, the colors make it easier to see if there is any liquid splashed or spilled in wrong places where they could potentially cause contamination, microwell sealing problems etc. Especially with adhesive sealing films applied on microtiter plates before thermal cycling, any liquid in the sealing contact can compromise the seal and thus the whole PCR assay.

The present invention can also be used together with the mechanical solutions to lower their error rate even more, if the pipetting steps performed are visualized using the colorants. When using pipetting robots, it is possible to add a quality check step based on optical detection after desired steps, or the volume and color of the reagents can be quickly checked visually.

For the above reasons, dyes and other colorants used in the present manner can help keeping track in reaction setup and especially during loading reagents into reaction plate. Thus, the approach provides considerable help and increased certainty for pipetting samples.

In qPCR there is no need to load the amplified products into a gel after a PCR reaction. Thus, a density enhancer is not needed. Consequently, the present solutions may be free of density enhancer or contain only minor amounts of density enhancer (i.e. less than required for gel electrophoresis).

According to one embodiment, there is provided, in addition to the abovementioned first and second reagent solutions, one or more additional reagent solutions comprising additional colorants providing the solutions different colors. The solutions are capable of forming, on mixing, additional solutions having, due to said additional colorants, further distinguishable colors. Thus, the invention can be used not only for aiding the pipetting in one particular stage of the process, e.g. pipetting of the of the sample to master mix, but also for aiding the pipetting during other steps, in particular the steps previous or subsequent to the sample pipetting step.

In more detail, the method may comprise providing a third reagent solution comprising at least one further substance required for performing said assay, the third reagent solution containing a third colorant providing the solution a fourth color different from the first, second and third colors mentioned above, and mixing the third reagent solution with the first and second reagent solutions for providing a mixed reagent solution having, due to said first, second and third colorants, a fifth color different from the first, second, third and fourth colors. In particular, the first reagent solution may be a sample, the second reaction solution the master mix and the third reagent solution may be a primer solution. The order of application is not essential, unless otherwise defined in assay instructions.

Alternatively, to the above the method may comprise providing a third reagent solution containing third colorant providing the solution a fourth color different from the first, second and third colors, and individually mixing the first reagent solution with said second and third reagent solutions for obtaining first and second mixed solutions having third and fifth colors, respectively, different from each other and the first, second and fourth colors. For example, the second reagent solution may contain one set of primers and the third reagent solution may contain a second set of primers. In this embodiment too, the colors of all initial ingredients and all resultant mixtures are unique.

The two abovementioned embodiments can also be chained such that the second and third reagent solutions are ultimately individually mixed with a reagent solution which is itself prepared by mixing at least two different colored reagent solutions. Other kinds of combinations are possible too.

A "reagent solution" is any solution containing at least one reagent needed or advantageously used for PCR purposes. Most typical ingredients are polymerase, nucleotide, primer, ions, magnesium, other salt, pH buffering agent, dNTPs or fluorescent qPCR dye or probe, oligonucleotide, nucleic acid binding agent, a nucleic acid template. The reagent may also be other polymerase reaction additive, which has an influence on the polymerase reaction or its monitoring.

The term "sample solution" covers both buffered and non-buffered sample solutions which are still free of template or into which the template to be amplified using PCR has already been added, unless otherwise specified. The term "sample solution" is covered by the term "reagent solution".

The term "master mix" refers to a mixture of all or most of the ingredients or factors necessary for PCR to occur, typically all except for the template and primers which are sample and amplicon specific. Commercially available master mixes are usually concentrated solutions. A master mix may contain all the reagents common to multiple samples, but it may also be constructed for one sample only. Using master mixes helps to reduce pipetting errors and variations between samples due to differences between pipetted volumes. It also minimizes the time spent for pipetting.

A qPCR master mix is a master mix intended for performing a qPCR reaction. Thus, it may contain fluorescent dye or fluorescently tagged oligonucleotide primers or probes.

The term "premix" refers to a master mix that contains all the necessary components for a PCR reaction except for the template.

The term "color" herein means any detectable spectral response (of a solution) to white light in the visual range. Thus, there is at least one wavelength range in the absorbance spectrum of the solution which provides a colored visual appearance for the solution (in contrast to the nearly 100% transmittance of water). White, black and shades of grey are herein counted as colors. As will be shown later, an absorbance higher than about 0.01 (1 mm light path) gives a visually perceivable color for a solution whereas an absorbance higher than about 0.001 (1 mm light path) can be relatively easily detected by hardware-based spectral detection means.

The term "different colors" means that the colors are distinguishable, preferably by the naked eye, but at least with spectral detection means. In particular, "different colors" may have maximum peaks in their absorption spectrum separated by at least 30 nm. Preferably, the different colors are selected from the groups of: red, yellow, blue or cyan, magenta, yellow and visually distinguishable combinations and shades thereof, such as green, orange, and violet.

The term "colorant" means any substance which is capable of being homogeneously mixed or dissolved within a solution and capable of giving the solution a perceivable color. According to one embodiment, the colorant is a dye, in particular an aqueous dye, preferably a non-oxidizing aqueous dye.

The terms "transparent" or "translucent" colorant-containing solution refers, in particular, to a solution which has an optical transmission window at at least some fluorescence excitation and/or emission wavelengths that can be used for performing qPCR, the wavelengths depending on the fluorophores, fluorescent dye(s), and/or modified DNA oligonucleotide probe(s) contained in the reaction mixture. Typically, the excitation wavelength is between 350 and 690 nm, in particular between 490 and 650 nm. The emission wavelength is typically between 350 nm-730 nm, in particular 515 nm-680 nm. A transparent solution is optically essentially non-diffusive, whereas a translucent solution passes light diffusely.

The term "sample" refers to a solid material or a solution that contains the nucleic acid of interest or is to be analyzed for the presence of nucleic acid of interest.

The term "dilution buffer" refers to a solution that can be used for sample pretreatment before PCR setup. Pretreatment can include sample lysis for releasing nucleic acids, dilution, binding, chemical lysis, precipitation and enzymatic digestion of some components.

The term "preparative process" refers to any reaction, pipetting step or pretreatment which yields a product which can in total or in part be used as a sample in a subsequent PCR reaction.

The term "dosing failure" should be interpreted broadly as comprising e.g. underdosing, overdosing, undesired sample component proportions and the presence of foreign substances or bodies in the sample space. "Correct dosing"

refers to a dosing which is acceptable for the assay concerned. The concept of "detection of a dosing failure" covers practical implementations using criteria for unacceptable dosing as wells as acceptable dosing.

The term "pipetting" covers manual pipetting, automatic pipetting and any other liquid-dispensing techniques equivalent to pipetting The term "wavelength channel" refers to a single wavelength or a band of wavelengths which can be distinguished from wavelength(s) of other wavelength channels by the measurement setup used.

Typically the third color, achieved by mixing the solutions with the first and second colorants, is a chromatic combination of the first and second colors of the solutions. Thus, the third color may be produced as a sum spectrum of the spectra of the first and second colors. However, it is not excluded that the third color is formed through a more complex process, e.g. reaction of the first and second colorants, or due to a fluorescent process, e.g. fluorescence resonance energy transfer (FRET), provided that the fluorescence wavelengths differ from those of qPCR fluorophores used.

Next, embodiments and advantages of the invention are described in more detail with reference to the attached drawings.

DETAILED DESCRIPTION OF EMBODIMENTS

To make plate setup easier, a dye combination is provided that helps keeping track of pipetting master mix, samples and mixing of these, in the pipetting phase of (q)PCR process. Thus, the dyes are preferably optimized so that they will have minimal effect on qPCR reaction (e.g. will not influence the sample or DNA polymerase used) and will not significantly affect optical detection of fluorescence. In other words, the dyes used are compatible with the qPCR assay.

Typical fluorophores used for qPCR purposes include Alexa 350, FAM™, TET™, VIC™, JOE™, HEX™, CY®3, TAMRA™, ROX™, Texas Red®, CY®5, CY®5.5 and Quasar®705, the emission and excitation wavelengths of which are shown in Table 1.

TABLE 1

| Dye | Ex | Em |
|---|---|---|
| Alexa 350 | 350 | 440 |
| FAM | 494 | 518 |
| JOE | 520 | 548 |
| VIC | 538 | 554 |
| HEX | 535 | 556 |
| Cy3 | 552 | 570 |
| TAMRA | 565 | 580 |
| Cy3.5 | 581 | 596 |
| Texas Red | 583 | 603 |
| ROX | 585 | 605 |
| Cy5 | 643 | 667 |
| Cy5.5 | 675 | 694 |
| Quasar705 | 690 | 705 |

Figure 1A:
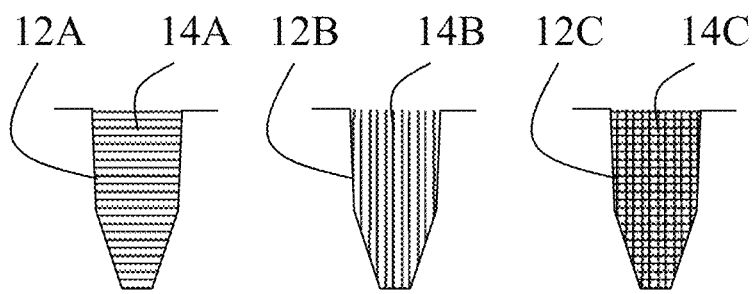
FIG. 1A shows in cross-sectional view three microwells containing colored sample buffer, colored reagent solution and their colored mixture, respectively.

FIG. 1A illustrates the basic principle of the invention. The microwell 12A contains colored sample buffer 14A having a first color (horizontal lines). The microwell 12B contains colored master mix 14B having a second color (vertical lines). The microwell 12C contains colored mixture of the sample buffer and colored master mix, having a third color (horizontal and vertical lines) resulting from the first and second colors.

Figure 1B:
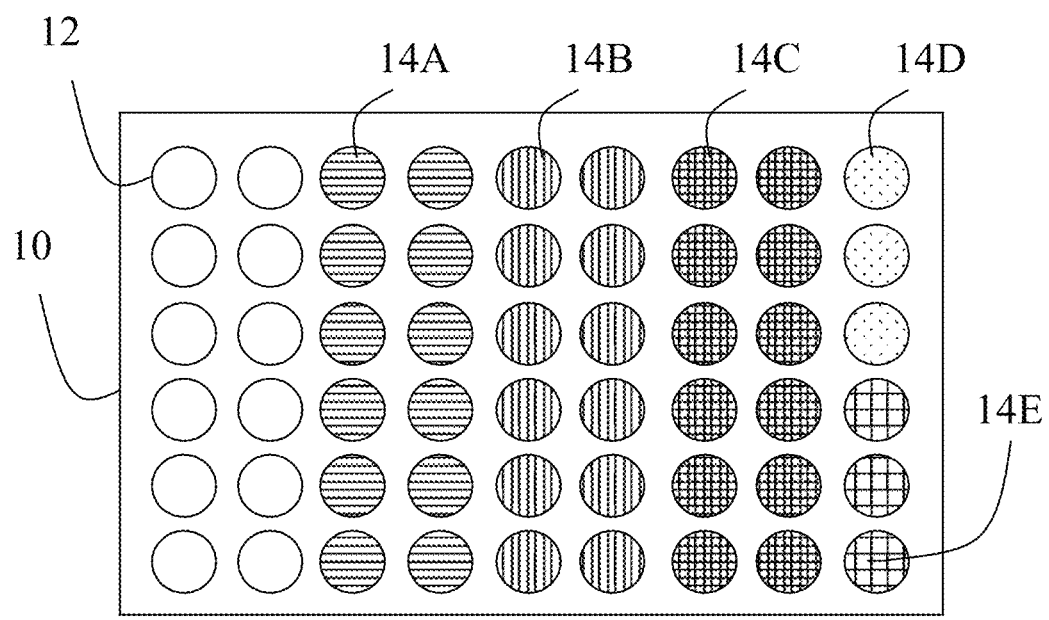
FIG. 1B shows a top view of a microtiter plate containing empty wells and wells containing colored sample buffer, colored reagent solution, their colored mixture and wells with optically clear liquid.

FIG. 1B illustrates a microtiter plate 10 which, in addition to the solutions shown and marked as in FIG. 1A, contains empty wells 12 and non-colored liquid 14D having no color (dots). In addition, there is shown a diluted reaction mixture 14E, which is achieved by diluting the initial reaction mixture 14C with the non-colored liquid 14D, the diluted reaction mixture having the same basic color as the initial reaction mixture 14C, but with increased transparency, i.e. reduced absorbance (sparse horizontal and vertical lines). As will be described later in more detail, not only the color, but also the degree of dilution can be monitored according to one embodiment of the invention.

The dyes can preferably be both detected and distinguished from each other visually, i.e. by naked eye. Thus, the different colors are spectrally relatively densely distributed and no special equipment is needed. However, in automatic devices utilizing optical spectral detectors or computer vision, also colors more finely distributed on the spectral scale can be used, without compromising the ability to distinguish between different colors.

According to one embodiment, the combination comprises a blue master mix and yellow sample buffer. When mixed together these form clearly green solution. Blue color in the plate indicates that master mix has been added but there is no sample yet. When sample is added color turns green. If solution in the well is yellow it means that there is only sample without mastermix. According to one embodiment, the blue dye comprises Xylene cyanol. According to one embodiment, the yellow dye comprises Quinoline yellow. These dyes have been found to be compatible with the polymerase and sample buffer, respectively.

Other potential dyes comprise Brilliant Blue, Patent Blue, Indigocarmine, Acid Red 1, m-Cresol Purple, Cresol Red, Neutral Red, Bromocresol Green, Acid Violet 5, Bromo phenol blue, and Orange G. Other potential dyes are listed in U.S. Pat. No. 6,942,964.

According to one embodiment, the dyes are strong enough to give a visually perceivable color for the respective solutions, but weak enough not to disturb fluorescence detection and/or weak enough not to interfere with gel electrophoresis migration tracking with other dyes commonly used for that purpose. For example, the abovementioned Xylene cyanol and Quinolene yellow belong to this group of dyes. Thus, if the colored amplified reaction mixture is subjected to end-point gel electrophoresis analysis, the colorants do not have an influence on the analysis. Instead of that, a conventional loading buffer with electrophoresis dye can be added to the amplified mixture. Moderate dyeing also maintains the general visual appearance of the solutions transparent or translucent.

A suitable concentration of the dye depends on the dye itself. According to one embodiment, directed to machine-aided color detection, the concentration of the dye in the initial solution is adjusted to result in an absorbance of 0.001-0.5 at its maximum absorption wavelength (1 mm light path). According to an embodiment directed to visual color detection, the concentration of the dye is adjusted to result in an absorbance of 0.01-0.5, in particular 0.03-0.5, at its maximum absorption wavelength (1 mm light path). According to a most preferred embodiment, the absorbance is 0.03-0.15, which ensures both visual detectability of the color and negligible or small effect on the qPCR measurement even if the absorbance peak would slightly overlap with the qPCR excitation and/or emission wavelengths. It is preferred, if such overlap exists, that the total absorbance at the qPCR excitation and/or emission wavelength is less than 0.05, preferably less than 0.03, in particular less than 0.01 (1 mm light path), regardless of the maximum absorbance. As the two (or more) initial solutions have differently colored dyes, there is no significant cumulative absorbance at any particular wavelength. It should also be noted that the above absorbances are the preferred absorbance of solutions diluted to the desired PCR processing concentration. If the solutions are delivered as concentrates, the preferred absorbances are respectively higher.

According to an alternative embodiment, at least one of the solutions is provided with dye, which is both suitable to be used in qPCR (i.e. does not affect the fluorescence detection at the wavelengths used) and strong enough to detected in gel electrophoresis, and runs on an appropriate distance at the gel with respect to the samples. Thus, a separate loading buffer is not necessarily needed.

The sample buffer containing a dye may be delivered either as a dilute or concentration, depending on the intended use.

Figure 2A:
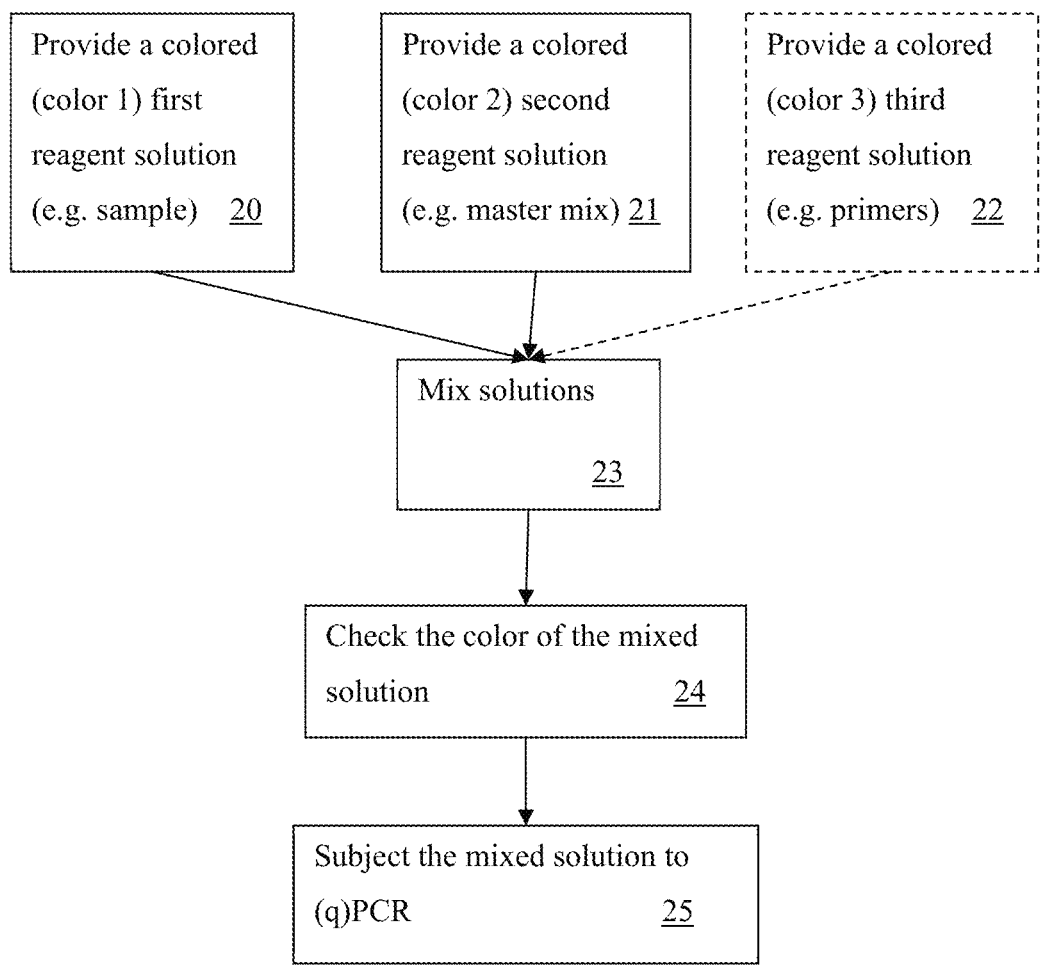
FIGS. 2A and 2B illustrate as a flow chart exemplary ways of carrying out the invention.

FIG. 2 illustrates the general concept of pipetting a colored sample solution (step 20) and at least one reagent solution (step 21, optionally 22) into a single container and mixing the solutions (step 23). The color of the mixed solution is checked (step 24) before subjecting the mixture to PCR (step 25). It should be noted that there may be other pipetting and processing steps which are not shown in FIG. 2 for simplicity.

Several embodiments taking advantage of the general idea of the invention are explained below.

According to one embodiment, there are provided a plurality of colored sample buffer solutions, in which different colorants are used to give the sample buffers different colors. According to a further embodiment, mixing the plurality of colored sample buffers with the same colored reagent mixture yields reaction mixtures of different colors. Thus, in a multi-sample PCR assay, one can distinguish between different samples based on the color of the solution. For example, a yellow sample buffer and a red sample buffer mixed with a blue master mix could give green and magenta reaction mixtures, from which one can immediately verify not only the proper mixing, but also the type of the sample.

According to one embodiment, there are provided a master mix and a plurality of colored primer mixes, in which different colorants are used to give the mixes different colors (master mix: color 1, primer mixes: color 2 and color 3). Combining the primer mixes with the mister mix yields still different colored mixes (colors 4 and 6). Further, by adding a colored sample (color 7) to the mixes obtained, distinguishable PCR solutions are obtained (colors 8 and 9). In each case of the process, the color of the solutions is indicative of the contents of the solution.

Figure 3:
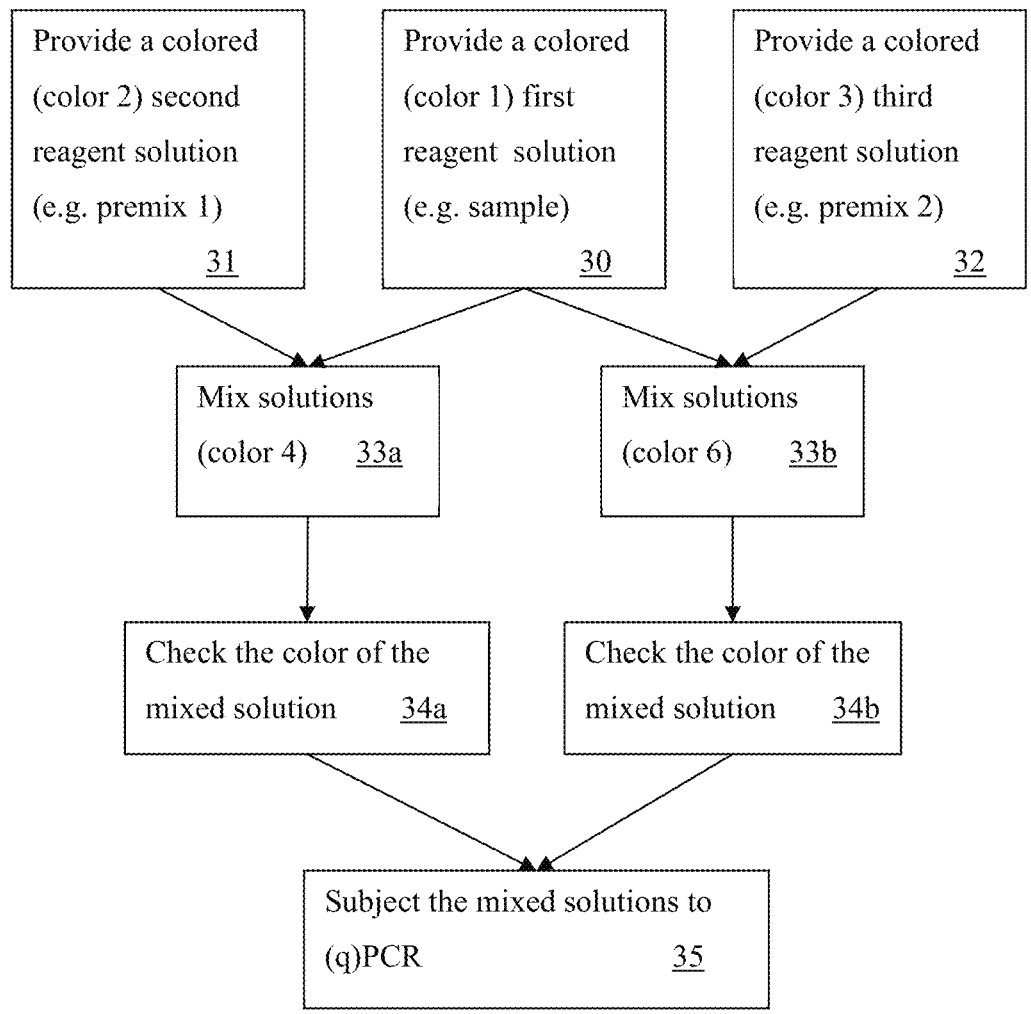
FIG. 3 shows a flow chart of the present process according to one embodiment of the invention.
Figure 4A:
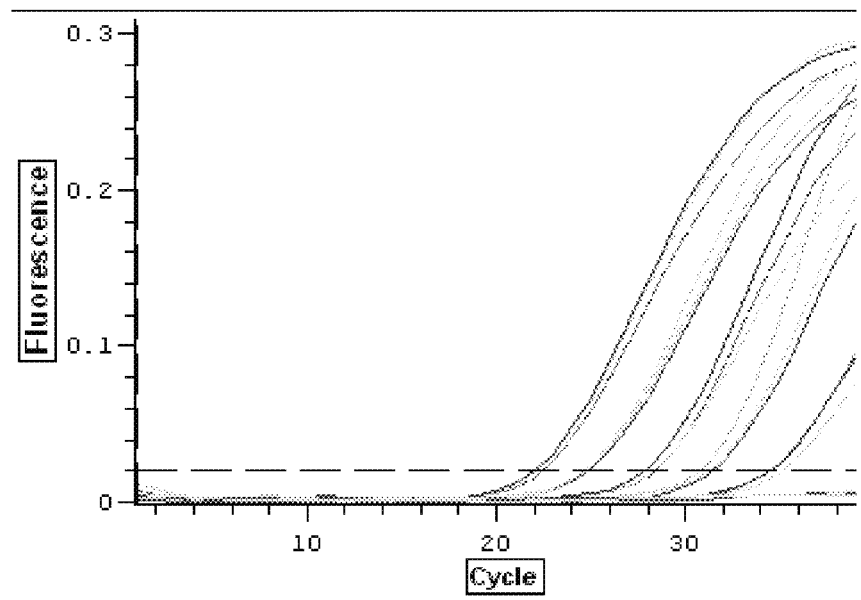
FIGS. 4A-4D show standard series obtained with master mix and sample with (4a and 4b) and without (4c and 4d) pipetting aid dyes.
Figure 4B:
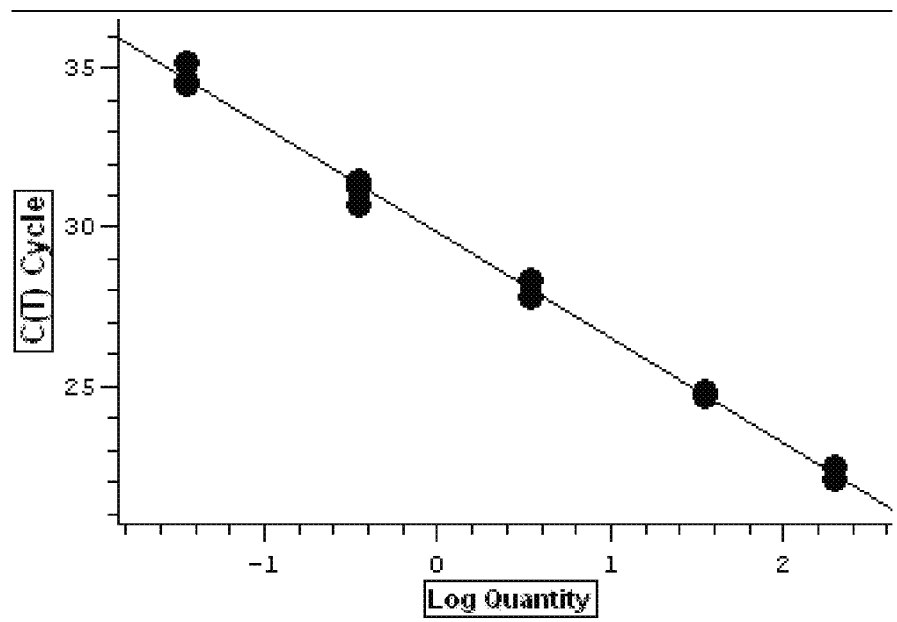
Figure 4C:
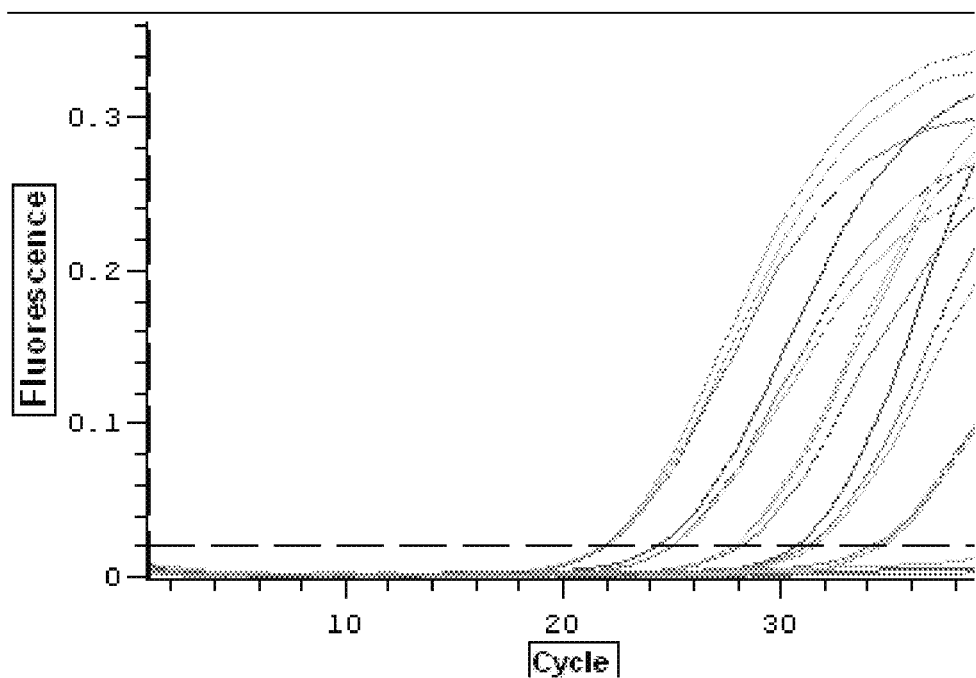
Figure 4D:
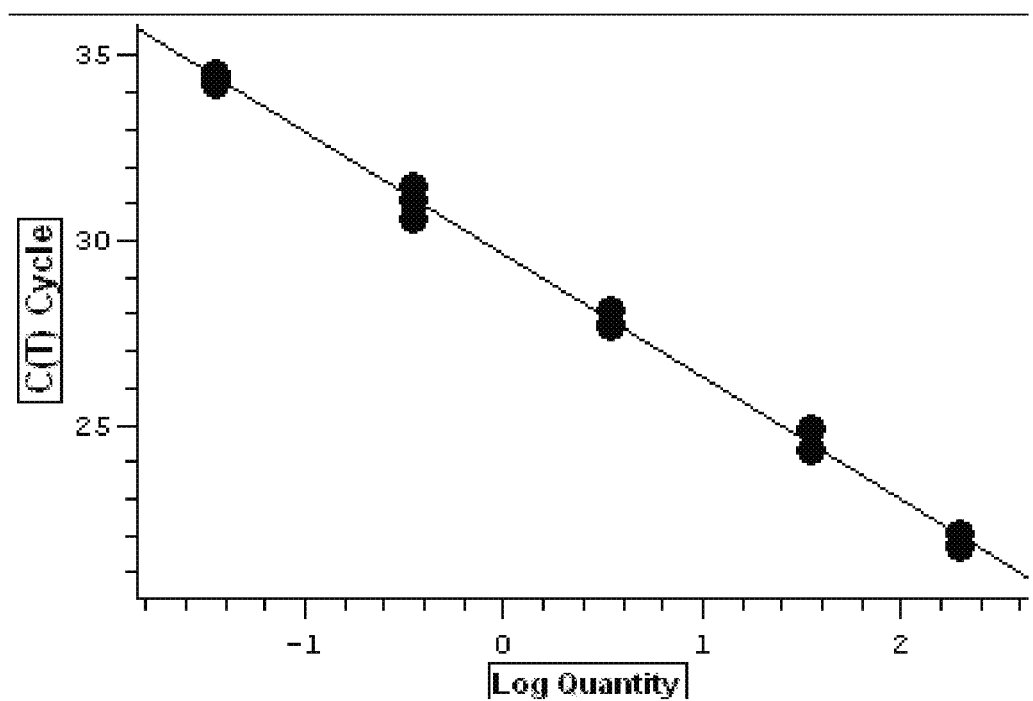

As illustrated in FIG. 3, according to one embodiment, there are provided a plurality of master mixes or other premixes (steps 31, 32) which are provided with different colorants to render the premixes differently colored (say, premix 1: color 2, premix 2: color 3, . . . premix n: color n+1) and a sample having a further color (color 1) (step 30). The premixes are individually mixed with the sample (steps 33a, 33b) and the colors of the resulting solutions are checked (steps 34a, 34b). The colors are preferably chosen so that each combination of a premix solution and sample solution solutions yields a unique color rendering the solutions distinguishable from each other and the initial premix and sample solutions. After checking (34a, 34b) the solutions are, in principle, ready for PCR. It should be noted that there may be other pipetting and processing steps which are not shown in FIG. 3 for simplicity.

More generally, there may be provided a plurality of initial solutions (each containing a component needed in the PCR reaction, e.g. polymerase, primer, ions, dNTPs or fluorescent qPCR dye or probe, or other additives) which are provided with different colorants to render the solutions differently colored (say, solution 1: color 2, solution 2: color 3, . . . solution n: color n+1) and a sample having a further color (color 1). The colors are preferably chosen so that each combination of solutions yields a unique color rendering the solutions distinguishable from the other solutions.

Selected variations of the invention having high utility value are described below.

Use of Dye in Elution Buffer

Nucleic acids for molecular biology experiments are usually purified from complex sample material. There are various methods for purification including methods based on extraction, precipitation, hybridization and different modes of chromatography or filtering etc. In most of the techniques nucleic acids are either dissolved or eluted in selected solution. Precipitated nucleic acids can be dissolved in a variety of solutions. When using other method that are based on other DNA interactions there are more requirements for the elution buffer such as suitable ionic strength. Purification methods based on DNA binding to silica in high ionic strength conditions are widely used. Bound DNA is eluted from silica matrix with low ionic strength buffer or with pure water. Many kits based on the silica binding method are available and usually the kit contains the elution buffer. To reduce the number of pipetting steps in the experiment workflow, the colorant can be included in the elution buffer or the buffer provided with the kit can be replaced with the colored buffer. By doing this, the user does not have to add the color in a separate step.

For example, the sample buffer containing the dye can be used as a sample elution buffer in combination with many commercial or homebrew DNA purification kits. The elution buffer provided with many of the available kits can be just simply replaced with the sample buffer containing the dye. Alternatively, a small amount of dye concentrate can be added in the elution buffer provided with the kit without diluting the sample too much.

The other colored reagent solution may be any other solution needed for the process, as discussed above.

Use of Dye in Dilution Buffer (Direct PCR)

New enzyme technology has made it possible to significantly simplify sample preparation for PCR and it is even possible to put the unpurified sample directly to the PCR. However in many experiments the sample needs to be separated in to several reactions and it is often preferable to be able to store some of the sample for possible repeats or other purposes. Thus direct PCR protocols where sample is lysed and dissolved in a special sample buffer are very popular. In these so called dilution protocols the dilution buffer may contain different agents that lyse the sample. In addition to these agents a colorant can be added to the dilution buffer to make subsequent pipetting steps easier.

The other colored reagent solution may be any other solution needed for the process, as discussed above.

To demonstrate this embodiment, two set of extractions from bovine milk samples were done with a kit based on DNA binding to silica. One following the guidelines and the other set where the elution buffer was replaced with 1× sample buffer with yellow dye. Purified samples were used in qPCR and qPCR results of the described two sets were compared. No significant difference was observed.

Use of Dye in Reverse Transcription Reaction

Majority of real time PCR is done for gene expression studies. In these experiments the nucleic acid of interest is RNA and thus not directly suitable template for normal qPCR. Before qPCR the RNA sample must be reverse transcribed before the qPCR step. Reverse transcription and qPCR reaction can be combined and performed subsequently in same reaction mixture. However usually the condition is a compromise and not optimal for either of the two reactions. In most cases it is more optimal to do separate reverse transcription reaction and use the created cDNA as a template in a separate qPCR reaction. In reverse transcription reaction setup there are the same challenges of keeping track of samples during pipetting as described for qPCR. An embodiment of the invention describes how colorant can be used in cDNA synthesis reaction to overcome this challenge.

The use of colorant in cDNA synthesis reaction has also been demonstrated as follows:

Two cDNA synthesis reaction series were prepared one with the yellow colorant, in final concentration of 10 fold compared to the concentration instructed for the qPCR, the other without the additional dye. HeLa total RNA dilution series with 1000 ng, 500 ng, 10 ng 1 ng, 100 pg and 10 pg dilutions were used as template. Reactions were otherwise done according to the manual (Product number F-470, Finnzymes). A 1.5 µl aliquot of each reaction was then used as a template in qPCR with DyNAmo SYBR Flash qPCR master mix.

With reference to FIGS. 6a-6c and 7a-7c, two standard curves were created, the first (FIG. 6c) representing the series with the added dye and the other (FIG. 7c) without the dye. The results show that cDNA synthesis can be performed in presence of colorant and the quantitative nature of the reaction is maintained.

In practice, the dye can be brought into the reaction with the transcriptase, with the sample, with the buffer solution or separately as a concentrate.

Use of Dye in Bisulphite Reactions

Similarly to what is discussed above, dye can also be added to any component taking part in a bisulphite treatment prior to mixing the sample thereby obtained with a second reaction solution.

As can be seen from the above examples, the dye can be present not only when mixing the final PCR reaction mixture but also in preparative process steps, in particular those relating to sample preparation, such as reverse transcription reaction (e.g. in cDNA synthesis), bisulphite reaction, sample elution or sample dilution. These examples are not limiting and, as understood by a person skilled in the art, the dye can be introduced also into these reactions in various ways, for example, with the enzyme, with reaction buffer, with the sample or separately.

As there is color present also in the preparative process steps, pipetting of these steps is facilitated too. However, according to a preferred embodiment, at least one colored solution is brought when mixing the final reaction solution, e.g. with the polymerase or master mix.

Figure 2B:
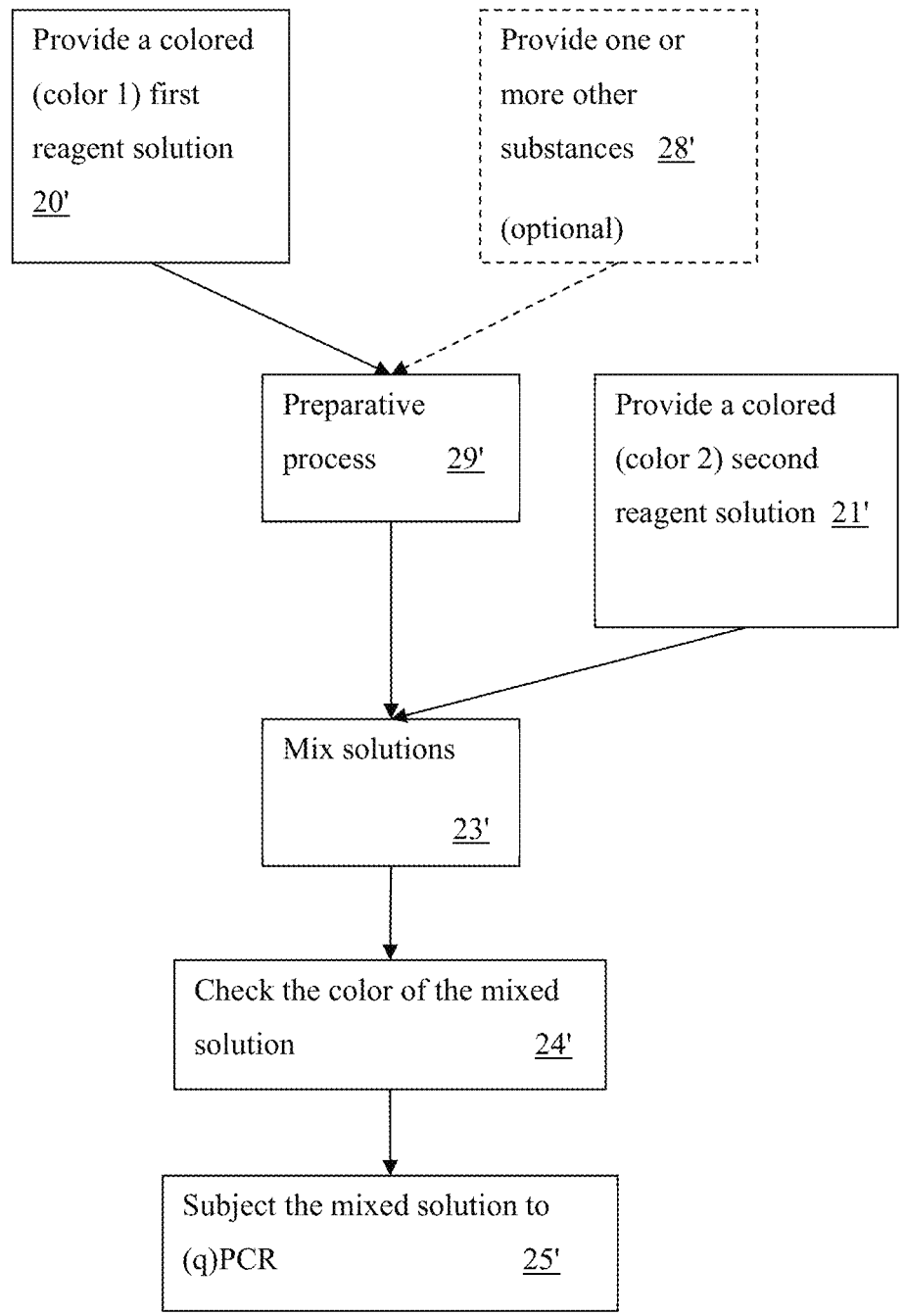

FIG. 2b illustrates, at a general level, the principle of introducing at least one colored reagent solution (step 20') to the process prior to at least one preparative process step 29'. The pretreatment may involve the introduction of one or more other substances too (step 28'). After pretreatment, the process can be continued similarly to as explained above, by mixing the product (or aliquot thereof) of the preparative process step with second colored reagent solution (steps 21' and 23'), checking the color of the mixed solution (step 24') and proceeding to (q)PCR (step 25').

Monitoring of the Pipetting Process

Preferably, the different colors are distinguishable by the naked eye. However, hardware-aided optical measurements capable of distinguishing between colors can be utilized too, irrespective of whether the colors are distinguishable by the naked eye.

Figure 8A:
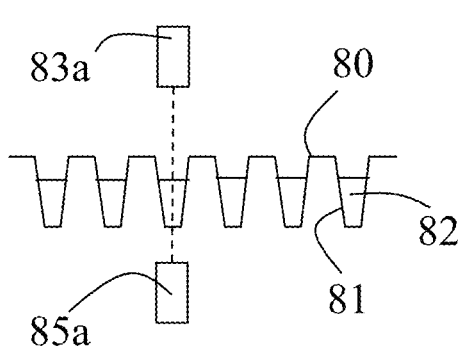
FIGS. 8A-8C illustrate exemplary measurement arrangements for detecting dosing failures.
Figure 8B:
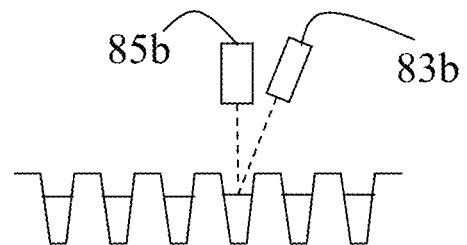
Figure 8C:
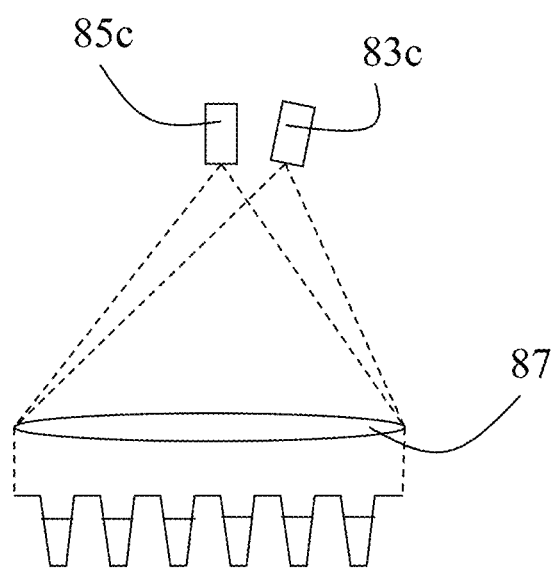

FIGS. 8a-8c show schematic examples of how the measurement can be carried out in an apparatus. The microtiter plate 80 having the microwells 81 is placed into a suitable plate holder (no shown). The samples 82 are pipetted in one or more steps to the microwells 81 before or after placement of the plate 80 to the holder. An absorbance measurement individually for each well can be carried out using a light source 83a and light detector 85a placed on opposite sides of the plate 80. A scattering measurement individually for each well can be carried out using a light source 83b and light detector 85b placed on the same side of the plate 80. Both measurement can be carried out for a plurality of wells simultaneously. As an example, a scattering measurement can be carried out using a light source 83b and camera 85b placed on the same side of the plate 80, the illumination and detection optionally taking place through a lens 87. The lens 87 can correct the perspective of imaging so that each well, irrespective of its position in the plate, is illuminated and imaged similarly to other wells.

The light source 83a-c and/or the detector 85a-c are in each of the embodiments can be a single- or multichannel device for being able to measure with spectral resolution.

The light source 83a-c and the detector 85a-c are in each of the embodiments connected to a control unit (not shows) controlling the measurement sequence. The detector is connected to a computing unit (not shown) for analyzing the measurement results and for making the decision on pipetting failures.

Further, there may be audial and/or visual means for signaling potential pipetting failures to the used or the apparatus or storage means (memory) for storing information of incorrectly pipetted microwells.

According to one embodiment, the condition of one or more microwells to be pipetted is checked at least once during the pipetting process automatically by optical means capable of spectral resolution.

According to one embodiment, the condition of the microwells is automatically checked at least two times in different stages of the pipetting process. Preferably such checking is carried out after every separate pipetting step.

The concentration of the colorant decreases and the color of a colored solution become weaker due to every addition of non-colored, i.e. optically clear, liquids. On the other hand, addition of colored substances changes the shade of the color. Thus, the strength and/or shade of color of a solution within a well is indicative of the stage of pipetting. By automatic measurement of the spectral response of the microwell(s), the progress of the pipetting process can be monitored.

According to one embodiment, the abovementioned monitoring is carried out using a computer program, which is adapted to compare the measured spectral responses after the desired pipetting steps with predefined limits for these steps. Such limits are designed to reflect the correct shade and/or strength of the color of the solution, taking into account the reagents added. A microwell, for which the measured value is not within an accepted range, is flagged incorrectly pipetted.

If the monitoring process is applied to an assay which necessitates sealing of the microwells using caps or film, for example, it is preferred that the optical measurements are carried out before sealing and/or after removal of the seal. Thus, optical reflections from the seal can be completely avoided. However, if the seal is transparent enough, the measurements can be carried out through the seal, too by a suitable method. In particular, fluorescence-based methods are insensitive to reflection effects from sealing layers.

Sealing is typically used at least in (q)PCR assays.

The detection of the color of a solution may be based on absorbance or transmission (photometric) measurement, scattering measurement or fluorescence measurement, to mention some examples. The detection instrumentation, which may be an integral part of an automatic pipetting apparatus or a (q)PCR thermal cycling apparatus, for example, contains suitable measurement means, i.e. a light source, a light detector and means for determining the desired optical response of the contents of a microwell at least at one wavelength or wavelength range.

In a qPCR instrument, the measurement equipment can be the partly or entirely the same as used during monitoring the PCR process.

According to one embodiment, the measurement means comprise a spectrophotometer configured for absorbance or transmission measurements.

In the case of PCR plate reading, it may however, be difficult to arrange good transmission photometric measurement conditions. This is because photometric measurement usually will need a good quality bottom window of microwells and the diameter of the window must be wide enough. Typically, PCR wells are very conical, whereby the bottom window area is small. In addition, in some cases the wells are non-transparent (typically white), which prevents transmission measurements. This is the case frequently in qPCR because white well color will enhance the qPCR fluorometric signal level compared with e.g. transparent wells. A white well wall enhances also other than PCR-related scattering measurements.

These problems can be solved by using scattered light measurement by illuminating the well from above and reading also from above. In the scattered light measurement there is no wavelength shift (as in fluorometry described below). Thus, the reading wavelength is same as the emission wavelength. White tube walls, if present, will scatter the light back to the detector so that color effect can be read.

According to one embodiment narrow-band light source (e.g. LEDs) and a monochrome detector (e.g. CCD or CMOS camera) are used. Color response is measured by illuminating the target sequentially by different bands using suitable control electronics.

According to one embodiment, a white light source (e.g. LED) and a color detector (e,g, CCD or CMOS camera) are used. This minimizes the need of control electronics.

Scattered light measurement can use visual filtering as in color camera case but also very color specific wavelength separation can be used. This is specially convenient with separate LEDs with monochrome camera.

A potential problem of scattered light measurement is that both the liquid surface and potential cover of the PCR plate will reflect back excitation light which can interfere the scattered light measurement. This problem can be avoided using fluorometric measurement where the excitation wavelength is filtered out so that reflection of liquid surface and cover of the well will not interfere liquid measurement.

If fluorescence colors are used, much lower concentration of the color components (dyes) are needed because of high fluorometric measurement sensitivity and potentially lower interference with actual qPCR-process.

Fluorescence detection will make system simpler in qPCR environment because it is more straightforward to tailor the fluorometer instrument for fluorometric color separation measurements.

According to one embodiment, the reflection problem is overcome using a scattering measurement utilizing polarization filter means arranged so as to eliminate or reduce the influence of light reflected from the surface of the sample on the measurement. In practice, this can be achieved using polarizing filters with different polarization properties in front of the light source and the detector. For example, if a linearly polarizing filter with S polarizing direction is arranged in front the light source and a linear polarizing filter with P polarizing direction (preferably 90 degrees rotated) is arranged in front of the detector, S-polarized light reflected from the surface of the sample cannot pass to the detector. However, light scattered from the sample and from the walls of the microwells is depolarized and the P-component of the depolarized light can be measured without an interfering signal from reflection.

According to one embodiment, a combination of a linear polarization filter and a circular polarization filter arranged in tandem (one after another) in the optical paths of the incident and reflected/scattered light is utilized. In this configuration, the linear polarizing filter will first polarize the incident light in a first linear direction. The circular polarizing filter will then give the light a circular polarization in a first circular direction. Light reflected from the sample will be circularly polarized in the opposite (second) circular direction. The circular filter will then polarize the reflected light in a second linear direction perpendicular to the first linear direction. Eventually, the linear polarization filter will not transmit this light. Depolarized scattered light, or suitable components thereof, will, however, pass the filters to the detector.

The above principles can be applied to camera based reading (full plate reading) and to single well reading. In singe well reading, instead of a 2D-camera, a silicon detector and 3 LEDs or a color sensitive silicon detector (for example three silicon detectors with filters) and a single LED can be used.

By means of the invention, the reliability of pipetting and PCR assay can be improved, as even small changes in shades and strengths of colors, and thus in the contents of the wells can be detected.

According to an alternative embodiment, the detection instrumentation is contained in a separate apparatus to which the reaction solutions can be transferred either automatically or manually after critical pipetting steps. In the separate apparatus, a quick plate read is carried out before the plate is transferred for further processing.

Thus, the invention also provides an apparatus for monitoring pipetting, comprising means for receiving a microtiter plate containing a plurality of microwells and means for measuring the optical absorbance of contents of the microwells. Said means for detecting the absorbance are adapted to detect the spectral absorbance profile of the sample (for color detection) and/or color intensity of the sample (for dilution detection). Preferably, the apparatus is capable of both the abovementioned functions for being able to monitor the entire pipetting process. The optical detection means are preferably connected to a computing unit which analyses and stores the measured absorbances and performs a calculation or comparison of the measurement data with pre-stored data.

The detection instrumentation may contain a microplate-receiving block which can be cooled for keeping the temperature of the reactions solutions low enough. For most hot-start polymerases cooling is not necessary.

Automatic detection is of particular assistance when the volume of the reaction vessel is small, that is, less than 5 µl, in particular less than 1 µl, as reliable visual observation of both the color and volume of the solutions is more difficult in these cases.

The microwells may be separate or be contained in microtiter strips or plates of any known type. Preferably, the wells are manufactured from transparent material, allowing the visual inspection or spectral measurements to be carried out through the wall of the well.

Dyeing Example

Xylene cyanol as a colorant was added to DyNAmo Flash SYBR® green qPCR and DyNAmo Flash Probe qPCR master mixes from (Finnzymes, Finland) in the concentration of 0.0026% (w/v). The result was a clearly blue transparent solution. Quinolene yellow was added to a sample buffer in the concentration of 0.00174% (w/v). The sample buffer contained 1 mM Tris-HCL pH 8.5 and 0.1 mM EDTA. As a result, a clearly yellow transparent solution was obtained.

The colored sample buffer and the colored master mix were mixed, resulting in a clearly green transparent mixture.

Amplification Example

FIGS. 4a-4d show standard series obtained with master mix and sample with (FIGS. 4a and 4b) and without (4c and 4d) the pipetting aid dyes of Example 1. Both series were done by amplifying human genomic DNA sequence with DyNAmo Flash Probe master mix according to the protocol in the product manual. Primer sequences were ACCTCCAAACTGGCTGTAAC and ATCTCCTCCTCATTGCAAAG. Detection was based on hydrolysis probe with a sequence TGGCCCCTTGAAGACAGCAG. Amplicon size was 121 bp.

From the mutual similarity of the amplification curves (FIGS. 4a and 4c) and standard curves (FIGS. 4b and 4d) can be seen that presence of the dye does not affect the reaction efficiency or significantly affect fluorescence intensities.

Pipetting Example

The present invention was utilized to implement the following pipetting sequence:
A colored (blue) 2× mix was thoroughly mixed with primers and probes, additives and water for obtaining a premix for several reactions.
The premix was pipetted to several wells of a microtiter plate (15 µl/well).
Colored (yellow) DNA sample solutions were pipetted onto the premixes (5 µl/well).
The color of the resulting solution was manually checked to be correct (green).

After the above steps, the resulting solution is ready to be subjected to (q)PCR. For qPCR, the reagents are preferably centrifuged to the bottoms of the wells.

Absorbance Measurement Examples

Absorbance of different dilutions of the dyes used in the examples above and dilutions of existing colored master mixes were measured and compared to visual observation to assess the visually perceivable range in different wavelengths. The purpose was in particular to determine visually perceivable absorbance range with different dyes and also check if commercially available dyes would be suitable to be used with FAM and SYBR fluorescent dyes which are probably the most popular dyes used in qPCR.

Measurements were performed with Nanodrop ND-1000 spectrophotometer, which uses 1 mm and 0.1 mm light paths.

The results, including visual detectability of color, absorbance maxima and absorbances of the samples as well as types of the solutions and dyes used in the experiments are shown in Tables 1-7 below. Tables 1-3 show the results obtained with preferred dyes to be used with FAM or SYBR, whereas Tables 4-7 show comparative examples obtained with commercially available colored PCR solutions.

In the Tables, the following denotations are used:
+++ strong color
++ color easy to see
+ weak color but visible in normal laboratory environment by naked eye
− color not visible in normal laboratory environment by naked eye For cases denoted with asterisk (*), the absorbance peak was not completely well-defined or clear.

TABLE 1

| Product | Dilution | Visual color | nm ($\lambda_{max}$) | $A_{(1\ mm)}$ | $A_{(1\ cm)}$ |
|---|---|---|---|---|---|
| Reagent color | 500x | +++ | 615 | | |
| Finnzymes | 50 x | +++ | 615 | 1.63 | |
| | 5x | ++ | 615 | 0.179 | |
| Xylene cyanol (XC) | 1x | ++ | 615 | 0.037 | 0.302 |
| | 0.5x | + | 615 | | |
| | 0.2x | − | 615 | | 0.013 |
| | 0.04x | | 615 | | |

Absorbance maximum (header spanning nm, $A_{(1\ mm)}$, $A_{(1\ cm)}$)

TABLE 2

| Product | Dilution | Visual color | nm ($\lambda_{max}$) | $A_{(1\ mm)}$ | $A_{(1\ cm)}$ |
|---|---|---|---|---|---|
| Sample buffer | 500x | +++ | 413 | | |
| Finnzymes | 50 x | +++ | 413 | | |
| | 5x | ++ | 413 | 0.578 | |
| Quinolene yellow | 1x | ++ | 413 | 0.124 | 1.163 |
| (QY) | 0.2x | + | 413 | 0.026* | 0.186 |
| | 0.04x | − | 413 | 0.022* | |
| | 0.02x | | 413 | | |

TABLE 3

| Product | Dilution | Visual color | nm ($\lambda_{max}$) | $A_{(1\ mm)}$ | $A_{(1\ cm)}$ |
|---|---|---|---|---|---|
| Colored reaction mix | 1x | ++ | 413 | 0.128 | |
| Finnzymes | 0.2x | + | 413 | 0.032 | 0.186 |
| | 0.1x | + | 413 | 0.015 | 0.059 |
| G7 | 0.04x | − | 413 | | |

Figure 5A:
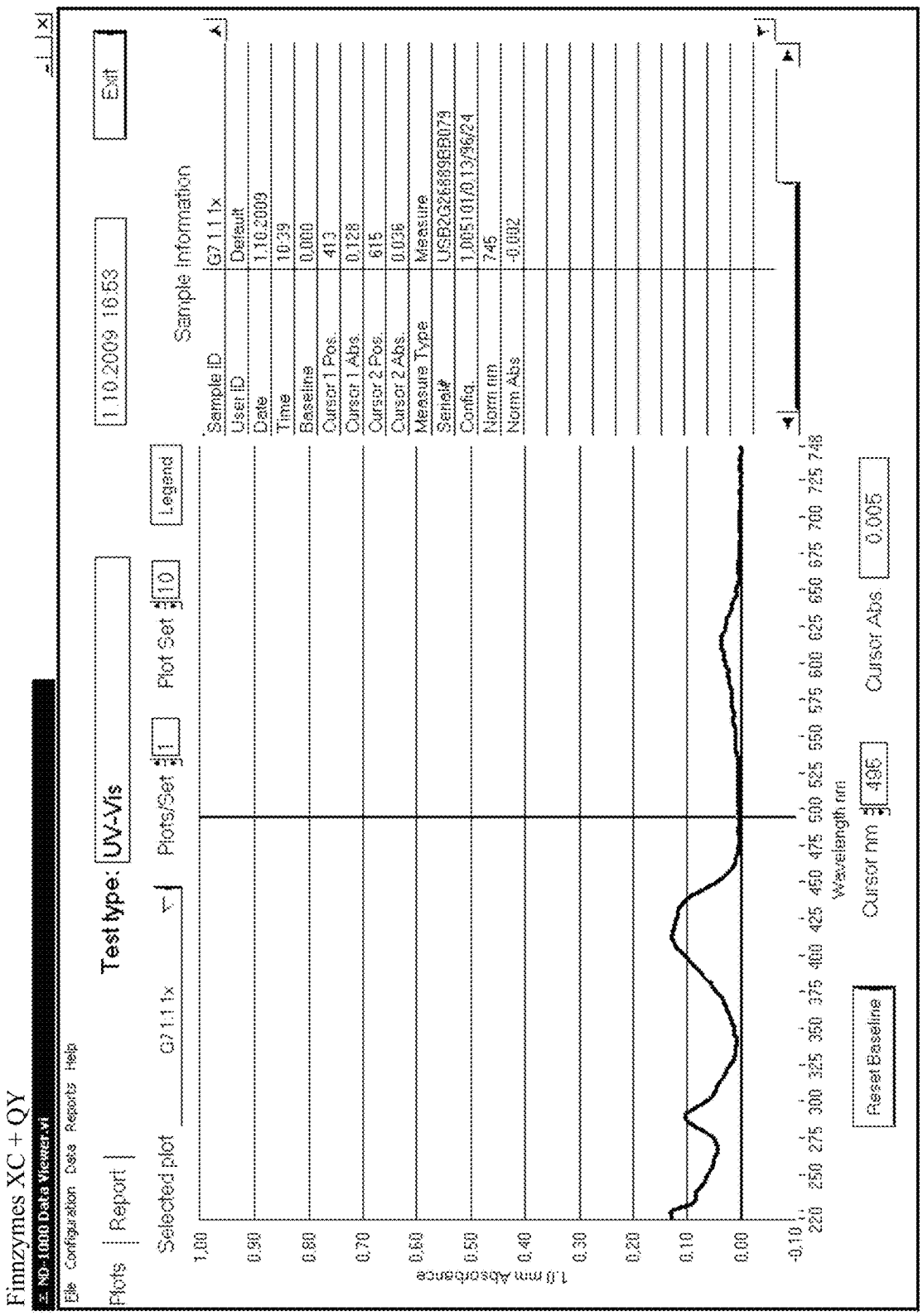
FIGS. 5A-5D show absorbance spectra relating to a absorbance measurement example.

The absorbance maxima of the solutions of Tables 1-3 are relatively far from the fluorescent wavelengths of FAM and SYBR dyes. The absorbance spectrum (1× dilution) of the reaction mixture of Table 3 is shown in FIG. 5a. From the data is can be concluded, that the dyes tested proved to be suitable to be used in the initial solutions and also together in a qPCR reaction mixture as colorants with these fluorescent dyes.

TABLE 4

| Product | Dilution | Visual color | nm ($\lambda_{max}$) | $A_{(1\ mm)}$ | $A_{(1\ cm)}$ |
|---|---|---|---|---|---|
| Crimson Taq buffer | 5x | +++ | 510 | 1.804 | |
| NEB | 1x | ++ | 510 | 0.406 | |
| | 0.5x | ++ | 510 | 0.213 | |
| CT | 0.1x | + | 510 | 0.046 | |
| | 0.02x | + | 510 | 0.013* | |
| | 0.01x | +/− | 510 | | |
| | 0.005x | − | 510 | | |

The buffer of Table 4 has absorbance maximum at 510 nm which is close to FAM and SYBR fluorescence maxima. Absorbance would decrease qPCR signals with these dyes significantly. Thus, the use of this mix in qPCR would not be feasible.

TABLE 5

| Product | Dilution | Visual color | nm ($\lambda_{max}$) | $A_{(1\ mm)}$ | $A_{(1\ cm)}$ |
|---|---|---|---|---|---|
| Green GoTaq | 5x | +++ | 419 | | |
| Promega | 1x | ++ | 419 | 1.183 | |
| | 0.5x | ++ | 419 | 0.527 | |
| GT | 0.1x | ++ | 419 | 0.130 | |
| | 0.02x | + | 419 | 0.029* | |
| | 0.01x | + | 419 | 0.014* | |
| | 0.005x | − | | | |

Figure 5B:
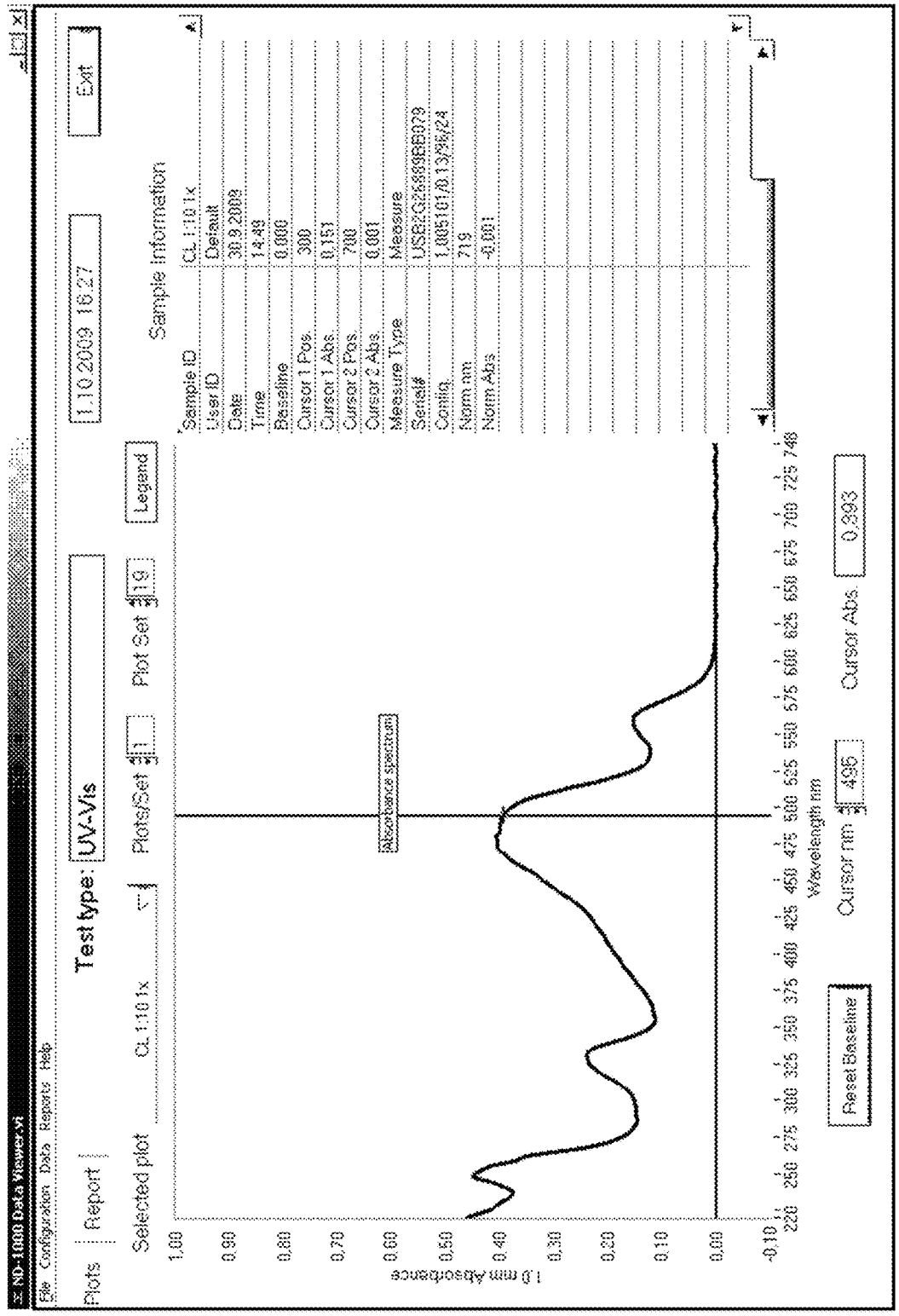
Figure 5C:
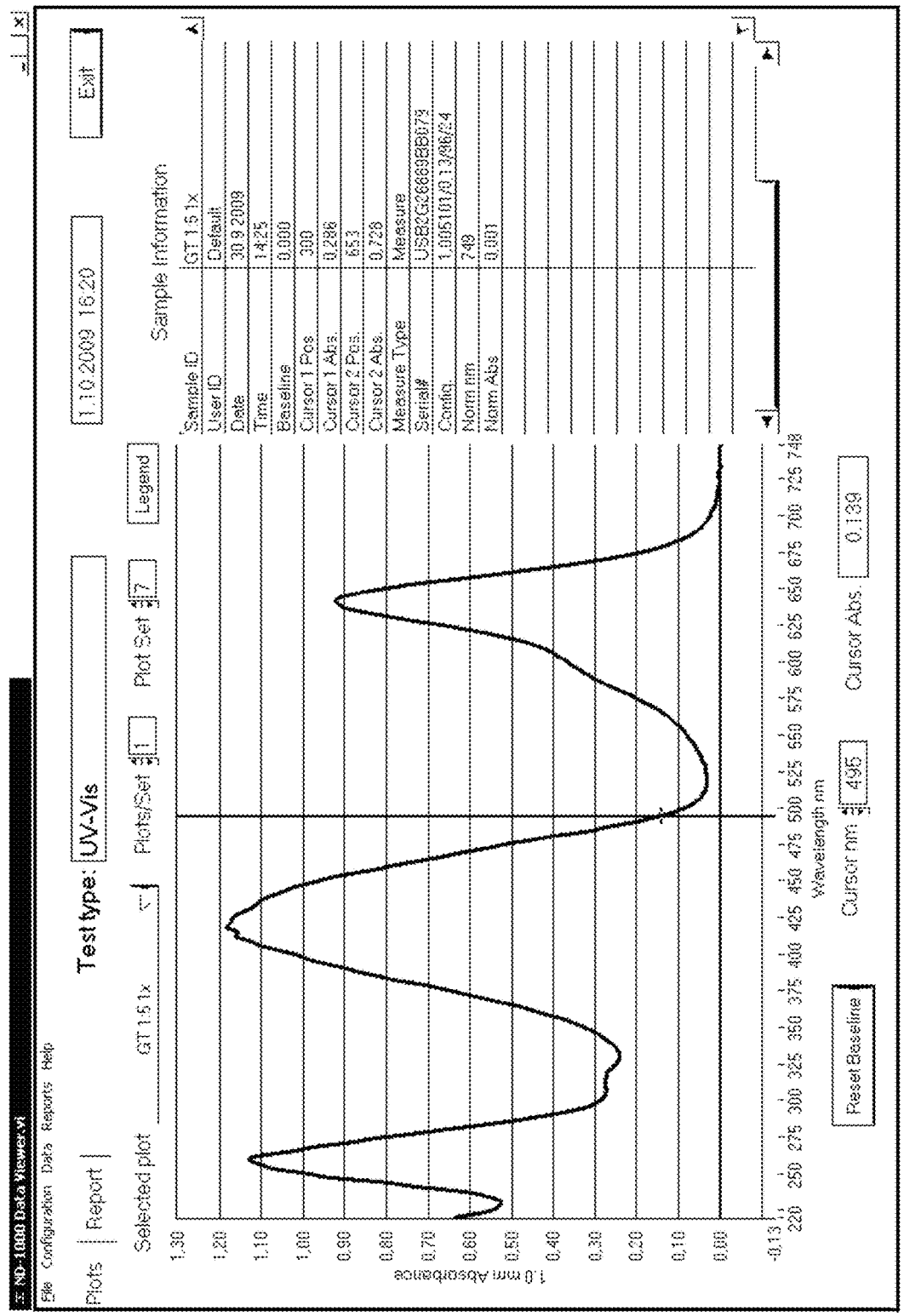

The mix of Table 5 has very strong absorbance at 419 nm. As the absorbance peaks are not very sharp it also has significant absorbance at 495 nm (0.17 with 1 mm light path), which is the range where FAM and SYBR dyes are excited. Absorbance would decrease qPCR signals with these dyes. The absorbance spectrum (1× dilution) is shown in FIG. 5c.

TABLE 6

| Product | Dilution | Visual color | nm ($\lambda_{max}$) | $A_{(1\ mm)}$ | $A_{(1\ cm)}$ |
|---|---|---|---|---|---|
| Quick-Load mm | 2x | +++ | 478 | 1.922* | |
| NEB | 1x | ++ | 485 | 1.000 | |
| | 0.5x | ++ | 485 | 0.516 | |
| QL | 0.1x | + | 485 | 0.103 | |
| | 0.02x | + | 485 | 0.025 | |
| | 0.01x | − | 485 | 0.012* | |
| | 0.005x | | | | |
| | 0.001x | | | | |
| | 0.0005x | | | | |

Figure 5D:
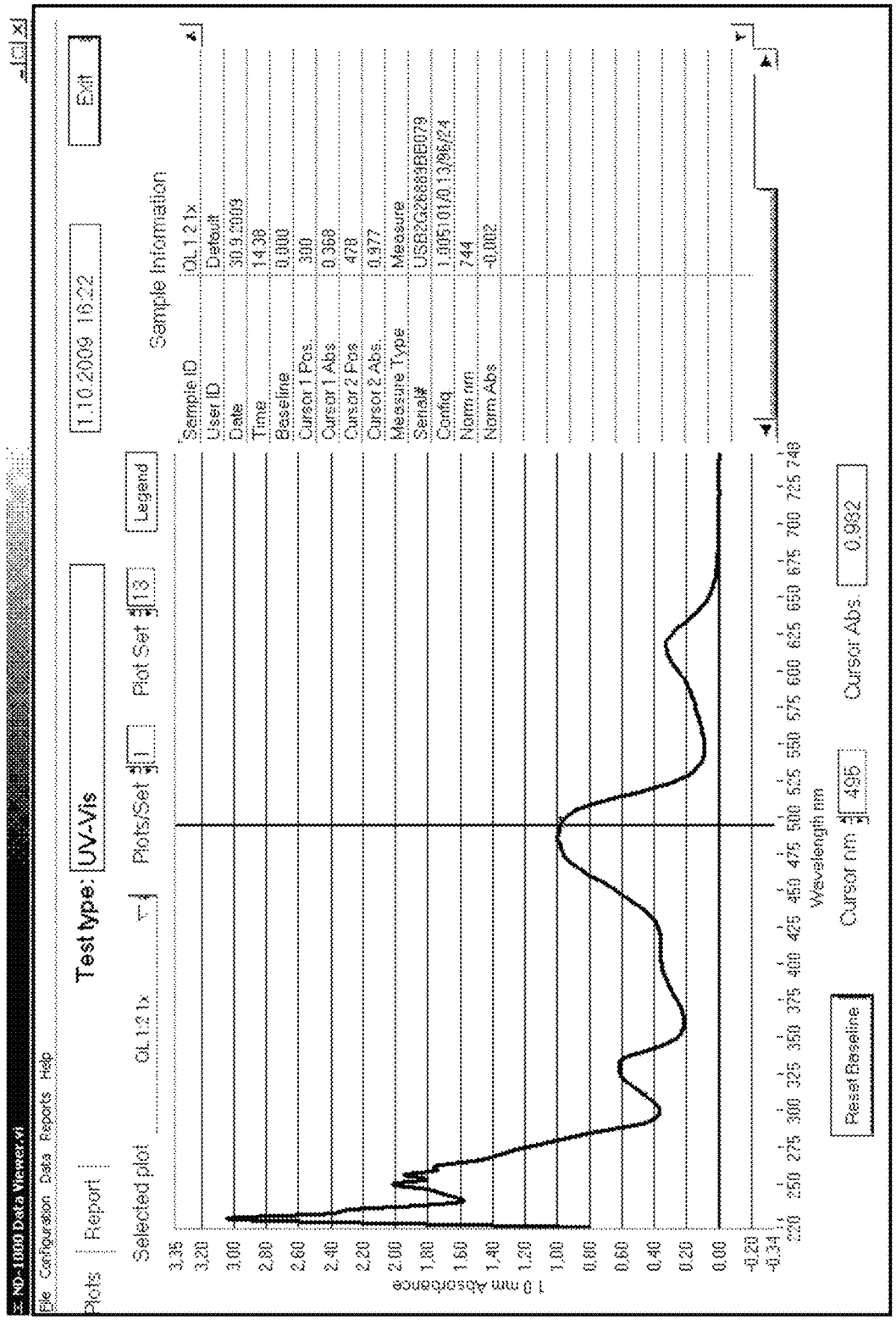
Figure 6A:
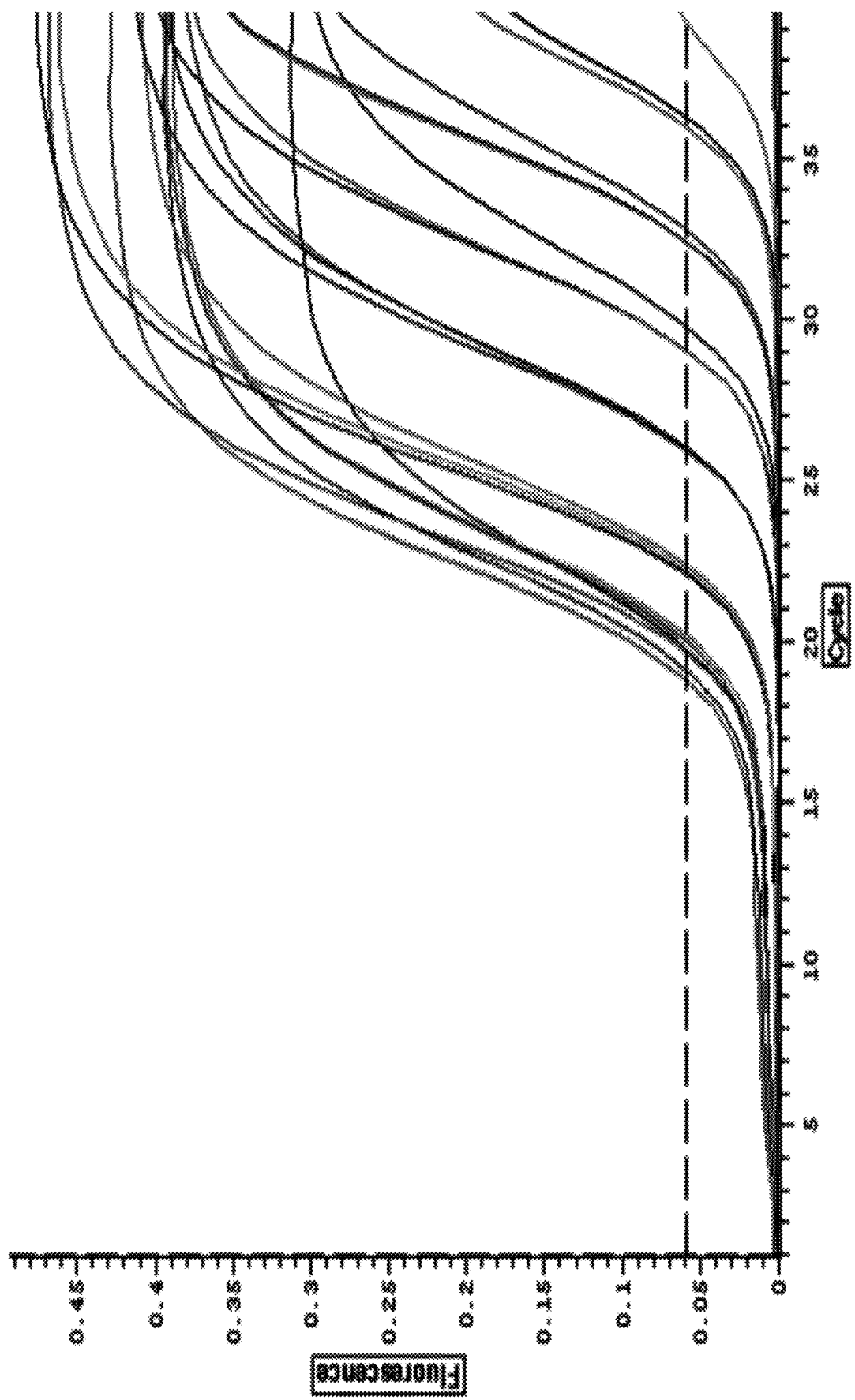
FIGS. 6A-6C and 7A-7C illustrate the use of colorant in a cDNA synthesis reaction.
Figure 6B:
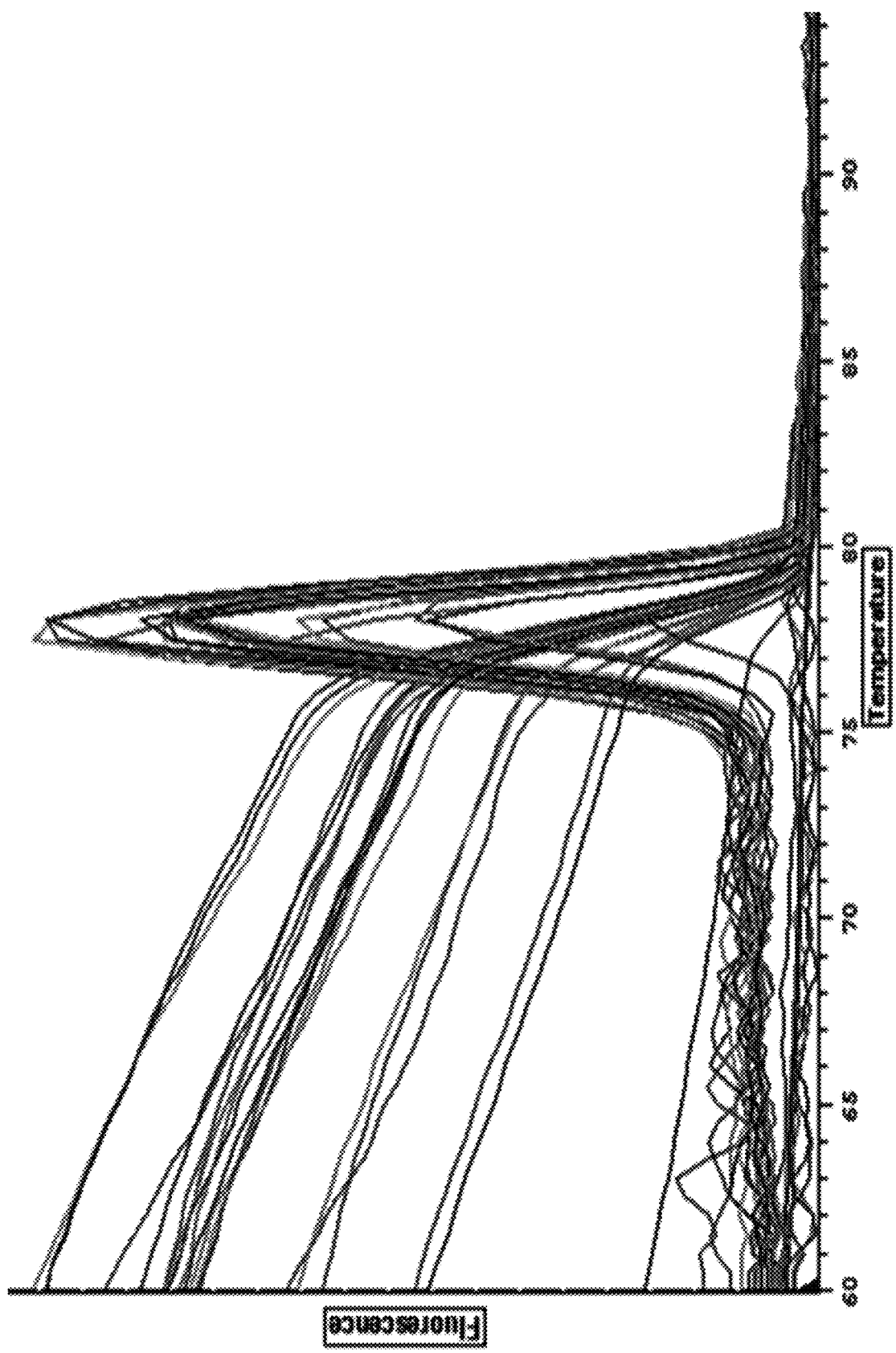
Figure 6C:
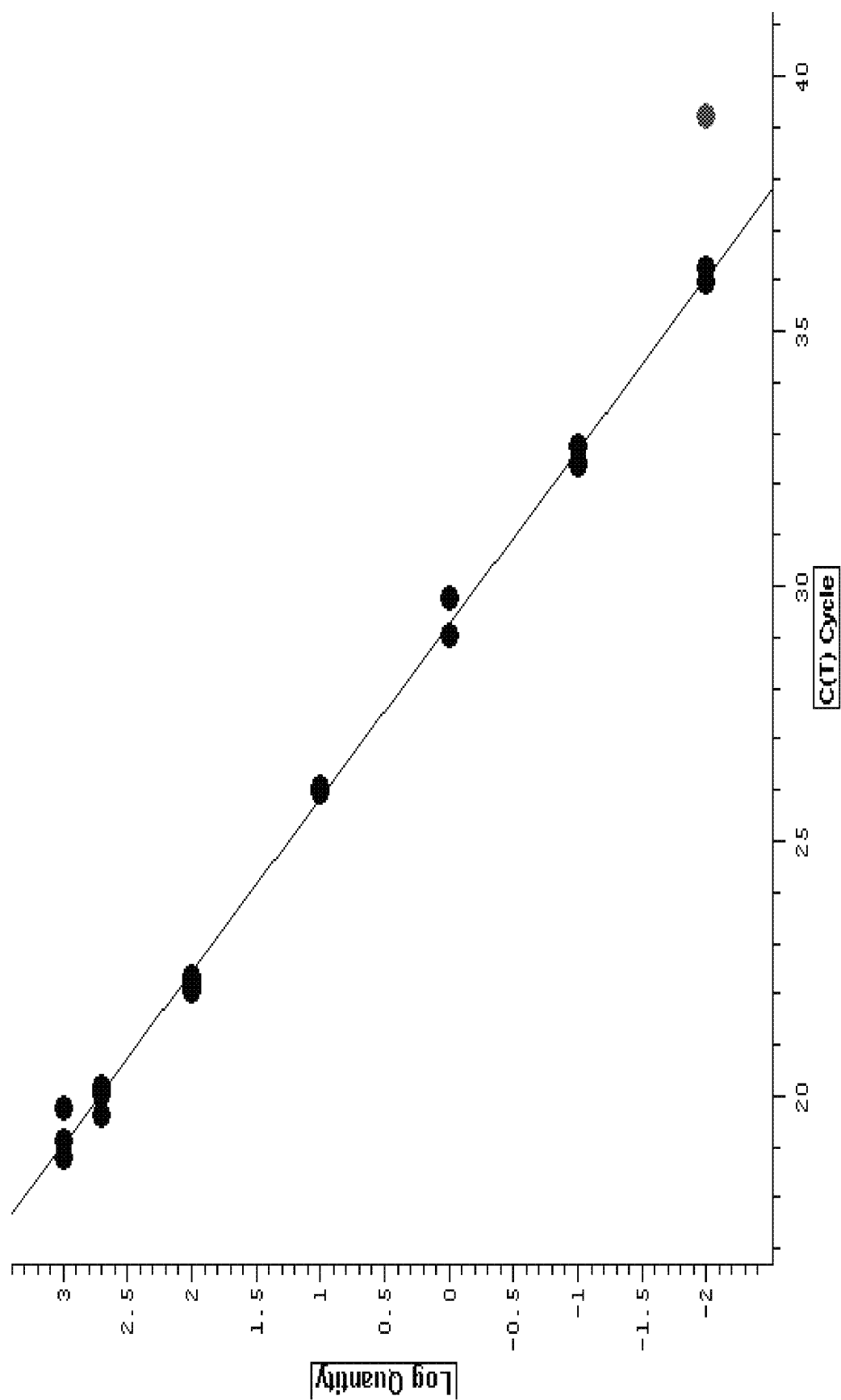
Figure 7A:
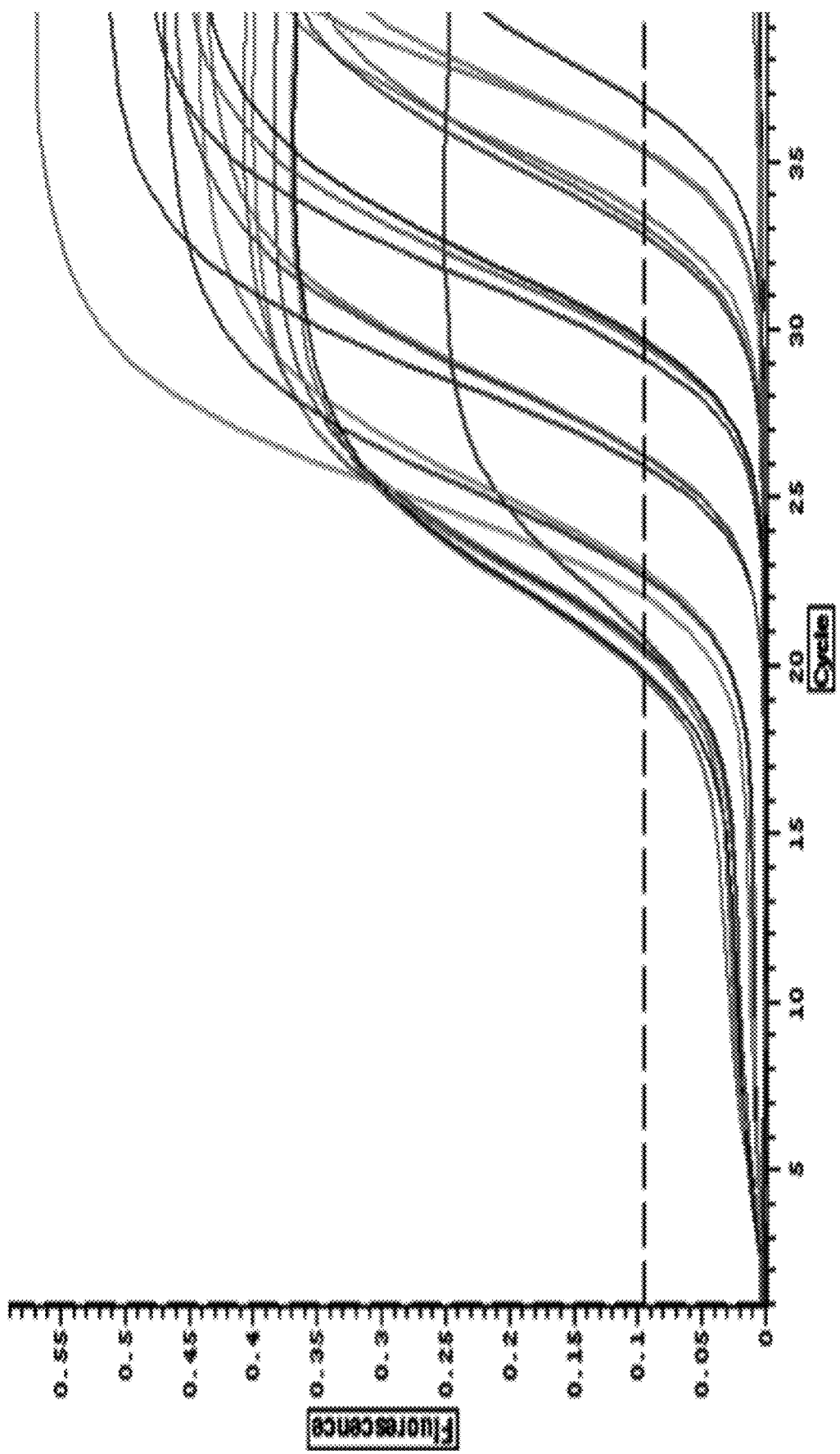
Figure 7B:
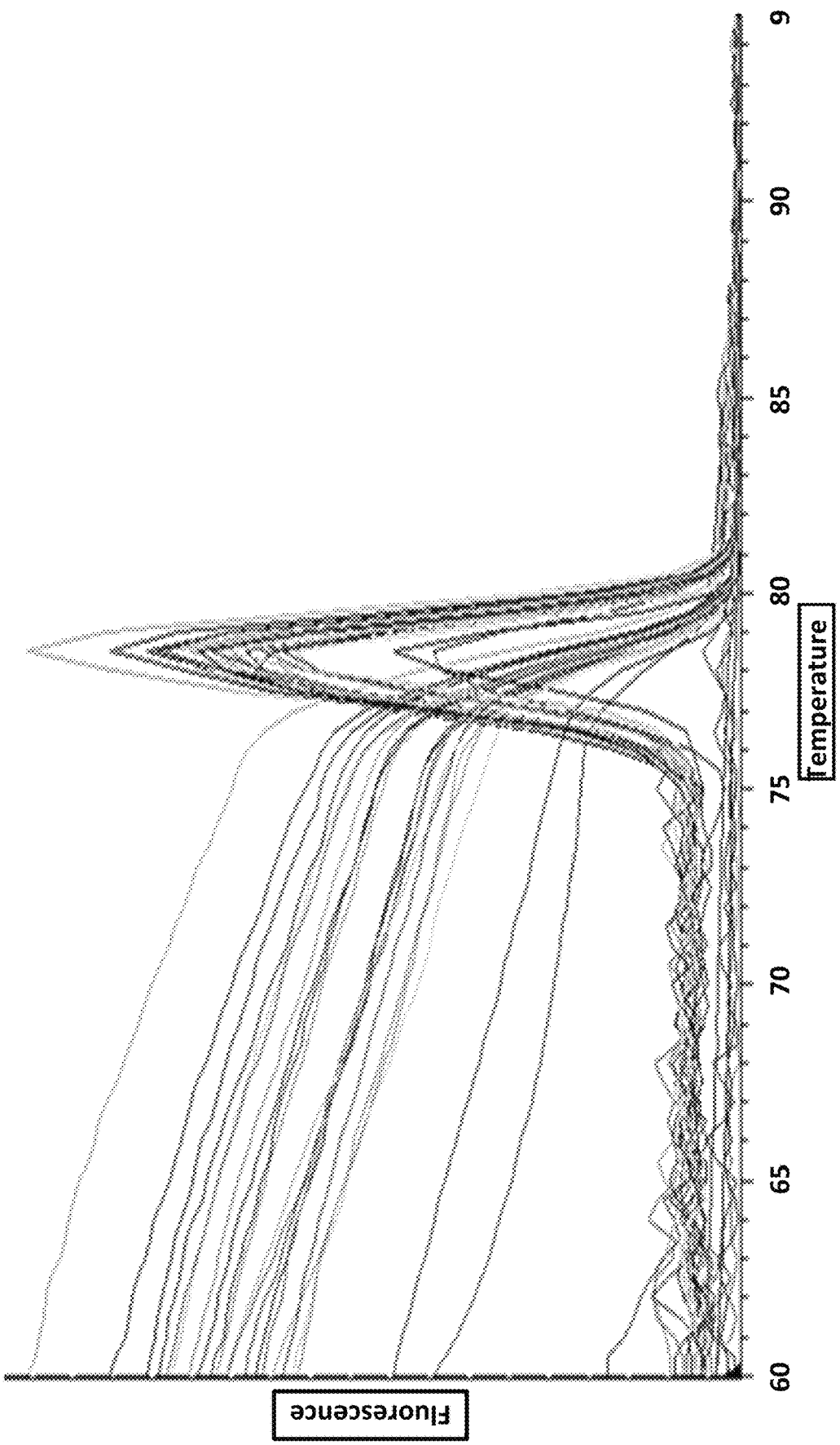
Figure 7C:
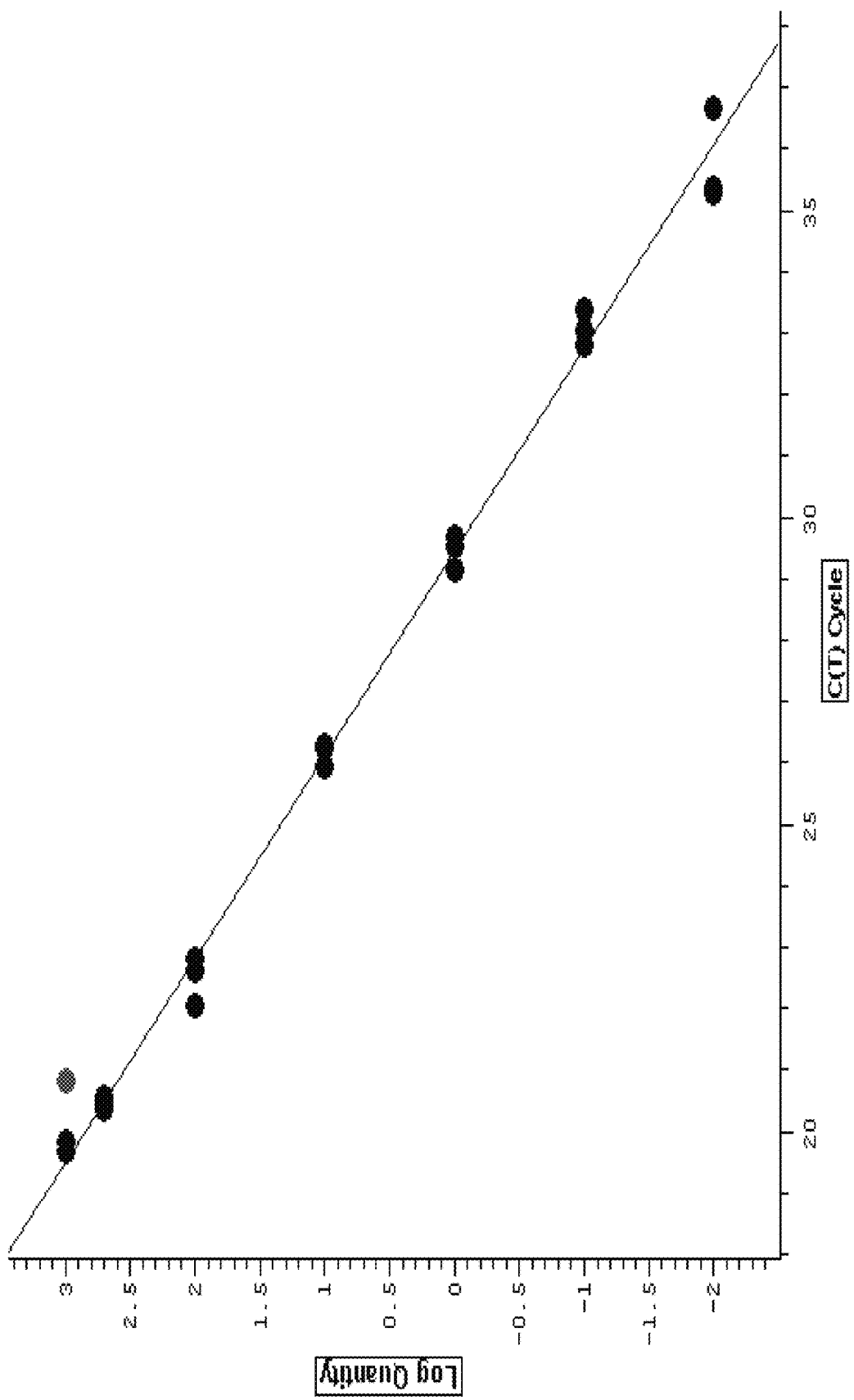

The mix of Table 6 has very strong absorbance at 485 nm. As the absorbance peaks are not very sharp it also has significant absorbance at 495 nm (0.982 with 1 mm light path), which is the range where FAM and SYBR dyes are excited. Absorbance would decrease qPCR signals with these dyes significantly. The absorbance spectrum (1× dilution) is shown in FIG. 5d.

TABLE 7

| Product | Dilution | Visual color | nm ($\lambda_{max}$) | $A_{(1\ mm)}$ | $A_{(1\ cm)}$ |
|---|---|---|---|---|---|
| Coral Load | 10x | +++ | | | |
| Qiagen | 1x | ++ | 475 | 0.407 | |
| | 0.5x | ++ | 475 | 0.202 | |
| CL | 0.1x | + | 475 | 0.043* | |
| | 0.04x | + | 475 | 0.018 | |
| | 0.02x | − | | | |

The mix of Table 7 has very strong absorbance at 475 nm. As the absorbance peaks are not very sharp it also has significant absorbance at 495 nm (0.393 with 1 mm light path), which is the range where FAM and SYBR dyes are excited. Absorbance would decrease qPCR signals with these dyes significantly. The absorbance spectrum (1× dilution) is shown in FIG. 5b.

Perceivable range is dependent on the wavelength but in general color providing a absorbance above 0.01-0.1 with 1 mm light path seems to be visually distinguishable from the clear liquid. When absorbance is raised to 0.1-0.2, the color appears very clear to the eye. However, sophisticated instruments are more sensitive and thus dyes providing absorbance above 0.001 could be used when e.g. a spectrophotometer, scattering detector or a fluorescence detector is used for color measurement.

Use of instrument for checking the reaction setup volume by color detection enables more diluted colors to be used for that purpose minimizing possible negative effects that the colors might have. For example in qPCR the range of dyes that could be used without significantly affecting fluorescence detection would be increased.

The embodiments and examples above and the attached drawings are for illustrative purposes. The scope of the invention should be evaluated on the basis of the following claims taking equivalents into account.

The invention claimed is:

1. A method of preparing a reaction mixture for Polymerase Chain Reaction (PCR) assay, comprising
    providing a first reagent solution comprising at least one substance required for performing said assay,
    providing a second reagent solution comprising at least one other substance required for performing said assay,
    mixing the first and second reagent solutions, providing a third reagent solution comprising at least one further substance required for performing said assay, mixing the third reagent solution with the first and second reagent solutions for providing a mixed solution to be subjected to the PCR process, characterized in that the first reagent solution contains a first colorant providing the first reagent solution a first color, the second reagent solution contains a second colorant providing the solution a second color different from the first color, said mixing of the first and second reagent solutions yields a mixed solution having, due to said first and second colorants, a third color different from the first and second colors, and wherein the third color is detected visually prior to subjecting the mixed solution to the PCR process, the third reagent solution contains a third colorant providing the solution a fourth color different from the first, second, and third colors, said mixing of the first, second, and third reagent solutions yields a mixed solution having, due to said first, second, and third colorants, a fifth color, different from the first, second, third, and fourth colors, the first or second reagent solution comprises an Alexa 350, FAM, JOE, VIC, HEX, Cy3, TAMRA, Cy3.5, Texas Red, ROX, Cy5, Cy5.5, Quasar705, or SYBR dye.

2. A solution set for Polymerase Chain Reaction (PCR) assay, comprising a first reagent solution comprising at least one substance required for performing said PCR assay, a second reagent solution comprising at least one other substance required for performing said PCR assay, a third reagent solution comprising at least one further substance required for performing said assay, characterized in that the first reagent solution is provided with a first colorant having a first color, the second reagent solution is provided with a second colorant having a second color different from the first color, the first and second reagent solutions are capable of forming, on mixing, a first mixed solution having, due to said first and second colorants, a third color different from the first and second colors, wherein the colors are capable of being detected visually, the third reagent solution contains a third colorant providing the solution a fourth color different from the first, second, and third colors, the first, second, and third reagent solutions are capable of forming, on mixing, a second mixed solution having, due to said first, second, and third colorants, a fifth color different from the first, second, third, and fourth colors, the first or second reagent solution comprises an Alexa 350, FAM, JOE, VIC, HEX, Cy3, TAMRA, Cy3.5, Texas Red, ROX, Cy5, Cy5.5, Quasar705, or SYBR dye.

3. The solution set according to claim 2, characterized in that at least one of said reagent solutions is a sample solution for receiving a template to be amplified.

4. The solution set according to claim 2, characterized in that at least one of the reagent solutions contains one or more of the following: polymerase, primer, ions or dNTPs or fluorescent qPCR dye or probe, preferably being a PCR master mix, in particular a qPCR master mix.

5. The solution set according to claim 2, characterized in that at least one of the reagent solutions is an elution buffer or a dilution buffer.

6. The solution set according to claim 2, characterized in that said first and/or second colorants are selected from the group of: Quinoline yellow, Xylene cyanol, Brilliant Blue, Patent Blue, Indigocarmine, Acid Red 1, m-Cresol Purple, Cresol Red, Neutral Red, Bromocresol Green, Acid Violet 5, Bromo phenol blue, and Orange G.

7. The solution set according to claim 2, characterized in that the concentration of said colorants in respective reagent solutions corresponds to absorbances of the said solutions at their maximum absorption wavelengths of 0.01-0.5, preferably 0.03-0.15 with 1 mm light path, when diluted to the desired PCR processing concentration.

8. The solution set according to claim 2, characterized in that the first reagent solution and/or the second reagent solution is a concentrate.

9. The solution set according to claim 2, characterized in that the first reagent solution and the second reagent solution are capable of forming a transparent or translucent mixed solution suitable for qPCR.

10. The solution set according to claim 2, characterized in that the first reagent solution is selected from: polymerase solution, polymerase buffer; and the second reagent solution is selected from: primers, probe and sample.

11. The solution set according to claim 2, wherein the absorbance peaks of any of said colorants do not overlap with the emission or excitation wavelength of the Alexa 350, FAM, JOE, VIC, HEX, Cy3, TAMRA, Cy3.5, Texas Red, ROX, Cy5, Cy5.5, Quasar705, or SYBR dye.

12. The solution set according to claim 2, characterized in that the total absorbance of the mixed solution at the emission or excitation wavelength of the Alexa 350, FAM, JOE, VIC, HEX, Cy3, TAMRA, Cy3.5, Texas Red, ROX, Cy5, Cy5.5, Quasar705, or SYBR dye is less than 0.05, preferably less than 0.03, in particular less than 0.1 (1 mm light path).

13. Use of the method according to claim 1, for preparing a reaction mixture for quantitative PCR.

14. Use of the solution set according to claim 1, for preparing a reaction mixture for quantitative PCR.

* * * * *